(12) United States Patent
Barenholz et al.

(10) Patent No.: US 8,895,054 B2
(45) Date of Patent: Nov. 25, 2014

(54) METHODS FOR JOINT LUBRICATION AND CARTILAGE WEAR PREVENTION MAKING USE OF GLYCEROPHOSPHOLIPIDS

(75) Inventors: Yechezkel Barenholz, Jerusalem (IL); Dorit Nitzan, Bargiora (IL); Izhak Etsion, Haifa (IL); Avi Schroeder, Moshav Massuot Yitzhak (IL); Grigory Halperin, Or-Akiva (IL); Sarit Sivan, Zichron Yaakov (IL)

(73) Assignees: Technion Research and Development Foundation Ltd., Haifa (IL); Hadasit Medical Research Services & Development Limited, Jerusalem (IL); Yissum Research Development Company of the Hebrew University of Jerusalem, Jerusalem (IL)

( * ) Notice: Subject to any disclaimer, the term of this patent is extended or adjusted under 35 U.S.C. 154(b) by 535 days.

(21) Appl. No.: 12/411,855

(22) Filed: Mar. 26, 2009

(65) Prior Publication Data

US 2010/0098749 A1    Apr. 22, 2010

Related U.S. Application Data

(63) Continuation-in-part of application No. PCT/IL2007/001215, filed on Oct. 7, 2007.

(60) Provisional application No. 60/847,651, filed on Sep. 28, 2006.

(51) Int. Cl.
| | | |
|---|---|---|
| *A61K 9/127* | (2006.01) | |
| *A61K 9/00* | (2006.01) | |
| *A61K 31/685* | (2006.01) | |
| *A61L 27/50* | (2006.01) | |

(52) U.S. Cl.
CPC ............... *A61K 31/685* (2013.01); *A61K 9/127* (2013.01); *A61K 9/0019* (2013.01); *A61L 27/50* (2013.01); *A61L 2430/24* (2013.01); *A61K 9/1271* (2013.01)
USPC ............................................................. 424/450

(58) Field of Classification Search
CPC ........................................................ A61K 9/127
USPC ........................................................... 424/450
See application file for complete search history.

(56) References Cited

U.S. PATENT DOCUMENTS

| | | | | |
|---|---|---|---|---|
| 5,304,380 | A | * | 4/1994 | Miyajima et al. ............. 424/450 |
| 5,403,592 | A | | 4/1995 | Hills |

(Continued)

FOREIGN PATENT DOCUMENTS

WO        02078445        10/2002

OTHER PUBLICATIONS

Forsey et al., (2006) The effect of hyaluronic acid and phospholipid based lubricants on friction within a human cartilage damage model. Biomaterials 27: 4581-4590.

(Continued)

*Primary Examiner* — Gollamudi Kishore
(74) *Attorney, Agent, or Firm* — Winston & Strawn LLP

(57) ABSTRACT

The present invention concerns methods of joint lubrication and/or prevention of cartilage wear making use of liposomes having membranes with at least one phospholipid (PL) of the group consisting of a glycerophospholipid (GPL) having two, being the same or different, $C_{12}$-$C_{16}$ hydrocarbon chain and a sphingolipid (SPL) having a $C_{12}$-$C_{15}$ hydrocarbon chain, the one or more membranes having a phase transition temperature in which solid ordered (SO) to liquid disordered (LD) phase transition occurs, the phase transition temperature being within a temperature of about 20° C. to about 39° C. for lubrication of joints.

17 Claims, 5 Drawing Sheets

(56) References Cited

U.S. PATENT DOCUMENTS

| | | | |
|---|---|---|---|
| 6,133,249 A | 10/2000 | Hills | |
| 6,538,032 B1* | 3/2003 | Namgoong et al. | 514/642 |
| 6,800,298 B1 | 10/2004 | Burdick et al. | |
| 7,749,485 B2* | 7/2010 | Tournier et al. | 424/1.21 |
| 2003/0139344 A1* | 7/2003 | Hung et al. | 514/12 |
| 2005/0069576 A1* | 3/2005 | Mills et al. | 424/450 |
| 2005/0123593 A1* | 6/2005 | Thompson et al. | 424/450 |
| 2005/0164981 A1* | 7/2005 | Burdick et al. | 514/54 |
| 2006/0029655 A1 | 2/2006 | Barenholz | |
| 2006/0147511 A1 | 7/2006 | Panzner | |
| 2010/0098749 A1* | 4/2010 | Barenholz et al. | 424/450 |
| 2011/0171288 A1* | 7/2011 | Mohammadi et al. | 424/450 |
| 2012/0213844 A1* | 8/2012 | Huang et al. | 424/450 |
| 2014/0079774 A1* | 3/2014 | Brinker et al. | 424/450 |

OTHER PUBLICATIONS

Hills and Crawford (2003) Normal and prosthetic synovial joints are lubricated by surface-active phospholipid: a hypothesis. J Arthroplasty 18(4): 499-505.
Hills et al., (1998) Release of lubricating synovial surfactant by intra-articular steroid. Br J Rheumatol 37(6): 649-52.
Kawano et al., (2003) Mechanical effects of the intraarticular administration of high molecular weight hyaluronic acid plus phospholipid on synovial joint lubrication and prevention of articular cartilage degeneration in experimental osteoarthritis. Arthritis & Rheumatism 48(7): 1923-1929.
Akerman, et al., "Intra-Articular and Skin Surface Temperature of Human Temporomandibular Joint," *Scand. J. Dent. Res.* 95(6):493-498 (1987).
Alexander, "Idiopathic Osteoarthritis: Time to Change Paradigms?," *Skeletal Radiol.* 33(6):321-324 (2004).
Ballantine, et al., "The Effects of Lipid Depletion on Osteoarthritic Wear," *Wear* 253(3):385-393.
Barenholz, et al., "S. Quality Control Assays in the Development and Clinical Use of Liposome-Based Formulations in Liposome Technology," $2^{nd}$ Ed., *CRC Press* (1993).
Barenholz, et al.,"Structure and Properties of Membranes in Physical Chemistry of Biological Surfaces," *Phys. Chem. Biol. Interfaces* (2000).
Barenholz, "Relevancy of Drug Loading to Liposomal Formulation Therapeutic Efficacy," *J. Liposome Res.* 13(1):1-8 (2003).
Barnett, et al., "Absorption Into the Rabbit Articular Cartilage," *J. Anat.* 99(Pt 2):365-375 (1965).
Benz, et al.,"Lubrication and Wear Properties of Grafted Polyelectrolytes, Hyaluronan and Hylan, Measured in the Surface Forces Apparatus," *J. Biomed. Mater. Res. A.* 71A(1):6-15 (2004).
Biltonen, et al., "The Use of Differential Scanning Calorimetry As a Tool to Characterize Liposome Preparations," *Chem. Phys. Lipids* 64(1-3):129-142 (1993).
Briscoe, et al., "Boundary Lubrication Under Water," *Nature* 444:191-194 (2006).
Conaghan, et al., "Is Progressive Osteoarthritis an Atheromatous Vascular Disease?," *Ann. Rheum. Dis.* 64:1539-1541 (2005).
Ethell, et al., "The Synovial Response to Exogenous Phospholipid (Synovial Surfactant) Injected Into the Equine Radiocarpal Joint Compared With That to Prilocaine, Hyaluronan and Propylene Glycol," *New Zealand Veterinary Journal* 47(4):128-132 (1997).
Faure, et al.,"Determination of DMPC Hydration in the L(Alpha) and L(Beta') Phases by 2H Solid State NMR of D2O," *Febs Lett.* 405(3):263-266 (1997).
Garbuzenko, et al., "Effect of Grafted Peg on Liposome Size and on Compressibility and Packing of Lipid Bilayer," *Chem. Phys. Lipids* 135(2):117-129 (2005).
Grainger, et al.,"Medical Management of Osteoarthritis of the Knee and Hip Joints," *Med. J. Aust.* 180(5):232-236 (2004).
Hills, et al., "Surfactants Identified in Synovial Fluid and Their Ability to Act As Boundary Lubricants," *Ann. Rheum. Dis.* 43:641-648 (1984).
Hills, et al., "Enzymatic Identification of the Load-Bearing Boundary Lubricant in the Joint," *Br. J. Rheumatol.* 37(2):137-142 (1998).
Hills, et al., "Deficiency of Lubricating Surfactant Lining the Articular Surfaces of Replaced Hips and Knees," *Br. J. Rheumatol.* 37(2):143-147 (1998).
Hollander, et al., "Studies in Osteoarthritis Using Intra-Articular Temperature Response to Injection of Hydrocortisone," *Ann. Rheum. Dis.* 15(4):320-326 (1956).
Jones, et al., "The Effect of Surface Active Phospholipids on the Lubrication of Osteoarthritic Sheep Knee Joints: Wear," *Tribol. Lett.* 16(4):291-296 (2004).
Klein, "Mechanism of Friction Across Molecularly Confined Films of Simple Liquids," *Tribologyseries* 36:59-64 (1999).
Klein, "Molecular Mechanisms of Synovial Joint Lubrication," *J. Eng. Tribology* 220(8):691-710 (2006).
Lajeunesse, et al.,"Subchondral Bone in Osteoarthritis: A Biologic Link With Articular Cartilage Leading to Abnormal Remodeling," *Curr. Opin. Rheumatol.* 15:628-633 (2003).
Mabrey, et al., "Investigation of Phase Transitions of Lipids and Lipid Mixtures by High Sensitivity Differential Scanning Calorimetry," *PNAS* 73(11):3862-3866 (1976).
Maroudas, "Distribution and Diffusion of Solutes in Articular Cartilage," *Biophys. J.* 10(5):365-379 (1970).
Merkher, et al., "A Rational Human Joint Friction Test Using a Human Cartilage-On-Cartilage Arrangement," *Tribol. Lett.* 22(1):29-36 (2006).
Nitzan, et al., "TMJ Lubrication System: Its Effect on the Joint Function, Dysfunction, and Treatment Approach," *Compend. Contin. Educ. Dent.* 25(6):437-444 (2004).
Ogston, et al., "The Physiological Function of Hyaluronic Acid in Synovial Fluid; Viscous, Elastic, and Lubricant Properties," *J. Physiol.(Cambridge)* 119:244-252 (1953).
Oloyede, et al., "Consilidation Responses of Delipidized Cartilage," *Clin. Biomech.* 19:534-542 (2004).
Oloyede, et al., "Biomechanical Responses of Normal and Delipidized Articular Cartilage Subjected to Varying Rates of Loading," *Connective Tissue Research* 45(2):86-93 (2004).
Oncins, et al., "Study of Frictional Properties of a Phospholipid Bilayer in a Liquid Environment With Lateral Force Microscopy As a Function of NACL Concentration," *Langmuir* 21(16):7373-7349 (2005).
Parasassi, et al., "Cholesterol Modifies Water Concentration and Dynamics in Phospholipid Bilayers: A Fluorescence Study Using Laurdan Probe," *Biophys J.* 66(3 Pt 1):763-768 (1994).
Pickard, et al., "Investigation Into the Effects of Proteins and Lipids on the Frictional Properties of Articular Cartilage," *Biomaterials* 19(19):1807-1812 (1998).
Radin, "Who Gets Osteoarthritis and Why?," *J. Rheumatol. Suppl.* 70:10-15 (2004).
Raviv, et al., "Lubrication by Charged Polymers," *Nature* 425(6954):163-165 (2003).
Rhee, et al. "The Secreted Glycoprotein Lubricin Protects Cartilage Surfaces and Inhibits Synovial Cell Overgrowth," *J. Clin. Invest.* 115(3):622-631(2005).
Sarma, et al.,"Phospholipid Composition of Articular Cartilage Boundary Lubricant," *J. Orthop. Res.* 19(4):671-676 (2001).
Schrader, et al., "Compressibility of Lipid Mixtures Studied by Calorimetry and Ultrasonic Velocity Measurements," *J. Phys. Chem. B* 106(25):6581-6586 (2002).
Schwarz, et al.,"Surface-Active Phospholipid As the Lubricating Component of Lubricin," *Br. J. Rheumatol.* 37(1):21-26 (1998).
Schwarz, et al., "Deformation and Tribology of Multi-Walled Hollow Nanoparticles," *Europhys. Lett.* 50(6):762-768 (2000).
Shmeeda, et al., "Enzymatic Assays for Quality Control and Pharmacokinetics of Liposome Formulations: Comparison With Nonenzymatic Conventional Methodologies," *Methods Enzymol.* 367:272-292 (2003).
Stockwell, et al., "Changes in Permeability of Articular Cartilage With Age," *Nature* 201:835-836 (1964).
Swann, et al., "The Isolation and Properties of a Second Glycoprotein (LGP-II) From the Articular Lubricating Fraction From Bovine Synovial Fluid," *Biochem. J.* 179:465-471 (1979).

(56) References Cited

OTHER PUBLICATIONS

Swann, et al., "The Lubricating Activity of Synovial Fluid Glycoproteins," *Arthritis Rheum.* 24:22-30 (1981).

Swann, et al.,"The Molecular Structure of Lubricating Glycoprotein-I, The Boundary Lubricant for Articular Cartilage," *J. Biol. Chem.* 256(11):5921-5925 (1981).

Swann, et al., "The Lubricating Activity of Human Synovial Fluids," *Arthritis Rheum.* 27:552-556 (1984).

Thomas, et al., "Knee Joint Temperature Measurement Using a Differential Thermistor Thermometer," *Rheumatology* 19(1):8-13 (1980).

Tirosh, et al., "A. Hydration of Polyethylene Glycol-Grafted Liposomes," *Biophys. J.* 74(3):1371-1379 (1998).

Varju, et al., "Assessment of Hand Osteoarthritis: Correlation Between Thermographic and Radiographic Methods," *Rheumatology* 43(7):915-919 (2004).

Vecchio, et al., "Surfactant Treatment for Osteoarthritis," *Rheumatology(Oxford)* 38(10):1020-1021 (1999).

Watanabe, et al., "Ultrastructural Study of Upper Surface Layer in Rat Articular Cartilage by "In Vivo Cryotechnique" Combined With Various Treatments," *Med. Elect. Microsc.* 33(1):16-24 (2000).

Yoshida, et al., "Ultrastructural Study of Upper Surface Layer in Rat Mandibular Condylar Cartilage by Quick-Freezing Method," *Histol. Histopathol.* 19:1033-1041 (2004).

Yui, et al. "Inflammation Responsive Degradation of Crosslinked Hyaluronic Acid Gels," *J. Control. Release* 22:105-116 (1992).

\* cited by examiner

METHODS FOR JOINT LUBRICATION AND CARTILAGE WEAR PREVENTION MAKING USE OF GLYCEROPHOSPHOLIPIDS

FIELD OF THE INVENTION

This invention generally concerns liposomes and methods for their therapeutic use.

LIST OF PRIOR ART

The following is a list of prior art, which is considered to be pertinent for describing the state of the art in the field of the invention.

Hills, B. A. Phospholipid and propylene glycol based lubricant. U.S. Pat. No. 6,133,249, 1998.

Hills, B. A. Lubricant Composition for Rheumatism. U.S. Pat. No. 5,403,592, 1990.

Hills, B. A.; Monds, M. K., Enzymatic identification of the load-bearing boundary lubricant in the joint. Br. J. Rheumatol. 1998, 37, (2), 137-142.

Oloyede, A., Gudimetla, P., Crawford, R., Hills, B. A., Biomechanical responses of normal and delipidized articular cartilage subjected to varying rates of loading. Connective Tissue Research 2004, 45, (2), 86-93.

Ethell, M. T.; Hodgson, D. R.; Hills, B. A., The synovial response to exogenous phospholipid (synovial surfactant) injected into the equine radiocarpal joint compared with that to prilocaine, hyaluronan and propylene glycol. New Zealand Veterinary Journal 1999, 47, (4), 128-132.

Pickard, J. E.; Fisher, J.; Ingham, E.; Egan, J., Investigation into the effects of proteins and lipids on the frictional properties of articular cartilage. Biomaterials 1998, 19, (19), 1807-1812.

Kawano, T.; Miura, H.; Mawatari, T.; Moro-Oka, T.; Nakanishi, Y.; Higaki, H.; Iwamoto, Y., Mechanical effects of the intraarticular administration of high molecular weight hyaluronic acid plus phospholipid on synovial joint lubrication and prevention of articular cartilage degeneration in experimental osteoarthritis. Arthritis Rheum. 2003, 48, (7), 1923-1929.

Forsey, R. W.; Fisher, J.; Thompson, J.; Stone, M. H.; Bell, C.; Ingham, E., The effect of hyaluronic acid and phospholipid based lubricants on friction within a human cartilage damage model. Biomaterials 2006, 27, (26), 4581-4590.

Klein, J., Molecular mechanisms of synovial joint lubrication. J. Proc. Inst. Mech Eng., Part J: J. Eng. Tribology 2006, 220, (8), 691-710.

Burdick et al., Biological lubricant composition and method of applying lubricant composition. U.S. Pat. No. 6,800, 298.

International patent application publication No. WO2003/000190;

International patent application publication No. WO2004/047792;

International patent application publication No. WO2002/078445.

A complete list of prior art, which is referred to occasionally in the text below, appears at the end of the description before the claims. Reference to the publications will be made by indicating their number from the complete list of references.

BACKGROUND OF THE INVENTION

Joint dysfunctions affect a very large portion of the population. Sufficient biolubrication is a prerequisite for proper joint mobility, which is crucial for prevention and amelioration of degradative changes of the joint[1].

A common joint dysfunction is osteoarthritis, with prevalence exceeding 20 million in the United States alone[2]. The etiology of osteoarthritis is multifactorial, including inflammatory, metabolic and mechanical causes[3-5]. Among the list of risk factors involved are age, gender, obesity, occupation, trauma, atheromatous vascular disease and immobilization[1, 3-7], osteoarthritis may arise as a result of articular cartilage breakdown; or conversely, subchondral bone sclerosis may actually precede cartilage degeneration and loss[8, 9]. Once articular cartilage is injured, damage progresses[10].

Current treatment focuses on reducing overloading of joints, physical therapy, and alleviation of pain and inflammation, usually by systemic or intra-articular administration of drugs[11].

Articular cartilage forms a smooth, tough, elastic and flexible surface that facilitates bone movement. The synovial space is filled with the highly viscous synovial fluid (SF), containing hyaluronic acid (HA) and the glycoprotein lubricin[12-14]. HA is a polymer of D-glucuronic acid and D-N-acetylglucosamine, which is highly unstable and degrades under the inflammatory conditions of osteoarthritis[15, 16]. Lubricin is composed of ~44% proteins, ~45% carbohydrates and ~11% phospholipids (PL)[12-14], of which ~41% are phosphatidylcholines (PCs), ~27% phosphatidylethanolamines (PE) and ~32% sphingomyelins[17-19]. These PL are referred to as "surface-active phospholipids" (SAPL). The PE and PC of SAPL contain two hydrocarbon chains, one of which is the monounsaturated oleic acid (18:1).

Many studies are found in the literature on the effect of SAPL on joint friction, but only a few of them deal with wear. Due to problems of acquiring suitable human specimens and the complicated nature of the experiments, most of the studies addressing this issue used animal cartilage.

Boundary lubrication, in which layers of lubricant molecules separate opposing surfaces, occurs under loading of articular joints[17, 18, 20]. Several different substances have been proposed as the native boundary lubricants in articular cartilage. In the past, HA was thought to be the major lubricant[21], however, a recent tribiological study states that HA "by itself . . . is not responsible for the nearly frictionless boundary biolubrication found in articular cartilage", but may contribute to load bearing and wear protection[22]. Many reports have shown lubricin to play the major role in the lubricating properties of synovial fluid[12, 14, 19, 20, 23, 24]. Pickard et al[25] and Schwartz and Hills[19] demonstrated that phospholipids defined as surface active phospholipids (SAPL) of lubricin facilitate joint lubrication in articular cartilage.

Special wear experiments[58] were conducted on intact sheep knee joints of which some were injected with lipid solvent prior to the wear tests. The wear progression of the 'naturally worn' joints was compared with that of the 'artificially worn' dissolved lipid ones. It was found that severe depletion of the SAPL layer, which is strongly related to osteoarthritis, resulted in accelerated wear of the articular cartilage. It was concluded that the lipid layer acts as a boundary lubricant and is critically important to the proper functioning of synovial joints. In another wear test[59], artificially worn lipid-depleted sheep knee joints were injected with two concentrations of the phospholipid dipalmitoyl phosphatidylcholine (DPPC) and worn further. The results indicated that a solution of DPPC may decrease cartilage wear in synovial joints.

Cartilage surfaces of human osteoarthritis hip and knee joints, which were replaced by artificial ones, showed deficiency of the outermost lubricating layer of SAPL[60].

Hills et al.[17] demonstrated that osteoarthritis joints have a SAPL deficiency, and that injection of the surface-active phospholipid 1,2-dipalmitoyl-sn-glycero-3-phosphocholine (DPPC) into joints of osteoarthritis patients resulted in mobility improvement lasting up to 14 weeks[26] without major side effects[27]. In another study, utilizing a unique cryogenic cartilage preservation technique, Watanabe et al. observed lipidic globular vesicles on the surface of healthy cartilage, which are assumed to play a major role in lubrication[28]. Kawano et al.[29] and Forsey et al.[30], using animal models, have shown that use of high molecular weight HA (~2000 kDa) combined with DPPC improved lubricating ability. DPPC in the form of multilamellar vesicles (MLV) has a phase transition temperature in which solid ordered (SO) to liquid disordered (LD) phase transition occurs of 41.4° C.

U.S. Pat. No. 6,800,298 discloses dextran-based hydrogel compositions containing lipids, particularly phospholipids, for lubrication of mammalian joints.

International patent applications publications Nos. WO2003/000190[63], WO2004/047792[64] and WO2002/078445[65] describe liposomal formulations for intraarticular delivery of active ingredients, such as steroids so as to treat an inflammatory condition.

Recently, Klein et al.[31] summarized various issues of joint lubrication at the molecular level. They point to the potential role of highly-hydrated brush-like charged macromolecules at the surface of cartilage as major contributors to cartilage lubrication[31-33].

SUMMARY OF THE INVENTION

The present invention is based on the discovery of a liposomal platform for joint lubrication and on studies of the effect of different phospholipids (PL) compositions, liposomal sizes and lamellarity on joint friction and/or on cartilage wear, using a cartilage-on-cartilage apparatus that mimics articular joints.

Thus, in accordance with the invention, a novel formulation based on a liposome system comprising PL is proposed, for introduction into synovial joints in order to improve or restore joint mobility. It was been found that the novel liposomal platform is effective as a lubricant as well as for reducing cartilage wear.

Thus, in accordance with a first of its aspects, there is provided the use of liposomes comprising one or more membranes with at least one phospholipid (PL) of the group consisting of a glycerophospholipid (GPL) having two, being the same or different, $C_{12}$-$C_{16}$ hydrocarbon chain and a sphingolipid (SPL) having a $C_{12}$-$C_{18}$ hydrocarbon chain, the one or more membranes having a phase transition temperature in which solid ordered (SO) to liquid disordered (LD) phase transition occurs, the phase transition temperature being within a temperature of about 20° C. to about 39° C., the use being for lubrication and/or reducing wear rate of joints (cartilage) having a joint temperature which is above the phase transition temperature of the membrane.

In accordance with another aspect there is provided a method for lubricating a joint of a mammal, comprising: administering into a cavity of the joint having a joint temperature a therapeutically effective amount of liposomes comprising one or more membranes with at least one phospholipid (PL) of the group consisting of glycerophospholipid (GPL) having two, being the same or different $C_{12}$-$C_{16}$ hydrocarbon chain and a sphingolipid (SPL) having a $C_{12}$-$C_{18}$ hydrocarbon chain, the one or more membranes having a phase transition temperature in which solid ordered (SO) to liquid disordered (LD) phase transition occurs, the phase transition temperature being at a temperature of about 20° C. to about 39° C.; the phase transition temperature being lower than the joint temperature.

In accordance with yet another aspect there is provided a method for preventing or reducing a mammal's cartilage wear, comprising: administering into a cavity of the joint having a joint temperature a therapeutically effective amount of liposomes comprising one or more membranes with at least one phospholipid (PL) of the group consisting of glycerophospholipid (GPL) having two, being the same or different $C_{12}$-$C_{16}$ hydrocarbon chain and a sphingolipid (SPL) having a $C_{12}$-$C_{18}$ hydrocarbon chain, the one or more membranes having a phase transition temperature (Tm, the temperature in which the maximum change in the heat capacity during the phase transition from solid ordered (SO) to liquid disordered (LD) occurs), the phase transition temperature being at a temperature of about 20° C. to about 39° C.; the phase transition temperature being lower than the joint temperature.

It is of particular importance to note that the criteria above are cumulative criteria, namely, (a) that the liposomes comprise one or more membranes with at least one phospholipid (PL) of the group consisting of glycerophospholipid (GPL) having two (being the same or different) $C_{12}$-$C_{16}$ hydrocarbon chain and a sphingolipid (SPL) having a $C_{12}$-$C_{18}$ hydrocarbon chain, and (b) that this combination of lipids form a membrane with a phase transition temperature in which solid ordered (SO) to liquid disordered (LD) phase transition occurs at a temperature of about 20° C. to about 39° C. (the phase transition temperature being lower than the joint temperature).

Thus, for example, while 1,2-dipalmitoyl-sn-glycero-3-phosphocholine (DPPC) is encompassed within criteria (a) above, when used as a sole liposome forming PL, the membrane thus formed has phase transition temperature above 39° C. and thus DPPC was found to be ineffective in joint lubrication and cartilage wear prevention. Thus, DPPC alone is excluded from the scope of the present invention. The lack of effective lubricating/wear reducing effect of liposomal membrane composed of DPPC alone is exemplified hereinbelow.

By a still further aspect of the invention there is provided a pharmaceutical composition for joint lubrication and/or reducing wear rate of joints having a joint temperature and comprising a physiologically acceptable carrier and liposomes; the liposomes comprising one or more membranes with at least one phospholipid (PL) of the group consisting of glycerophospholipid (GPL) having two, being the same or different, $C_{12}$-$C_{16}$ hydrocarbon chains and a sphingolipid (SPL) having a $C_{12}$-$C_{18}$ hydrocarbon chain; the one or more membranes having a phase transition temperature in which solid ordered (SO) to liquid disordered (LD) phase transition occurs, the phase transition temperature being within a temperature of about 20° C. to about 39° C. and being below said joint temperature.

The GPL, SPL or their combination form liposomes, preferably liposomes with a mean diameter greater than about 0.3 μm, typically greater than about 0.5 μm and at times greater than about 0.8 μm. The mean diameter of the liposomes is usually less than about 10 μm, typically less than about 8, 7, 6 or 5 μm and at times less than 3.5 μm. The liposomes may be a single-membrane liposome or may be, according to one embodiment, multilamellar vesicles (MLV) liposomes. According to other embodiments the liposomes may also be large multivesicular vesicles (LMVV) or dehydrated rehydrated vesicles (DRV) liposomes.

In one embodiment said $C_{12}$-$C_{16}$ or $C_{12}$-$C_{18}$ hydrophobic chains are saturated.

The liposomal compositions of the invention may be administered to an afflicted joint through intra-articular injection, orthoscopic administration, surgical administration and in general any form of administration that can be used to instill such a formulation into the joint synovium or onto the joint cartilage. Afflicted joints treatable according to the invention may be associated with a variety of conditions, such as arthritis, rheumatoid arthritis, osteoarthritis (as well as osteoarthritis in rheumatoid arthritis patients), traumatic joint injury, sports injury, locked joint (such as in temporomandibular joint (TMJ)), status post surgical intervention such as arthrocentesis, arthroscopic surgery, arthroplasty, knee and hip replacement. A preferred condition to be treated or prevented by the invention is primary or secondary osteoarthritis.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 9A is a micrograph of healthy cartilage, showing its naturally occurring lipidic vesicle structures on the surface (x3000); FIG. 9B is a micrograph of arthritic cartilage (x3000); and healthy cartilage subjected to friction tests in the presence of the following lubricants: saline (x6000, FIG. 9C); ISF (x800 FIG. 9D); DMPC-SUV (x800, FIG. 9E); and DMPC-MLV (x6000 FIG. 9F).

DETAILED DESCRIPTION OF SOME NON-LIMITING EMBODIMENTS

Figure 1:
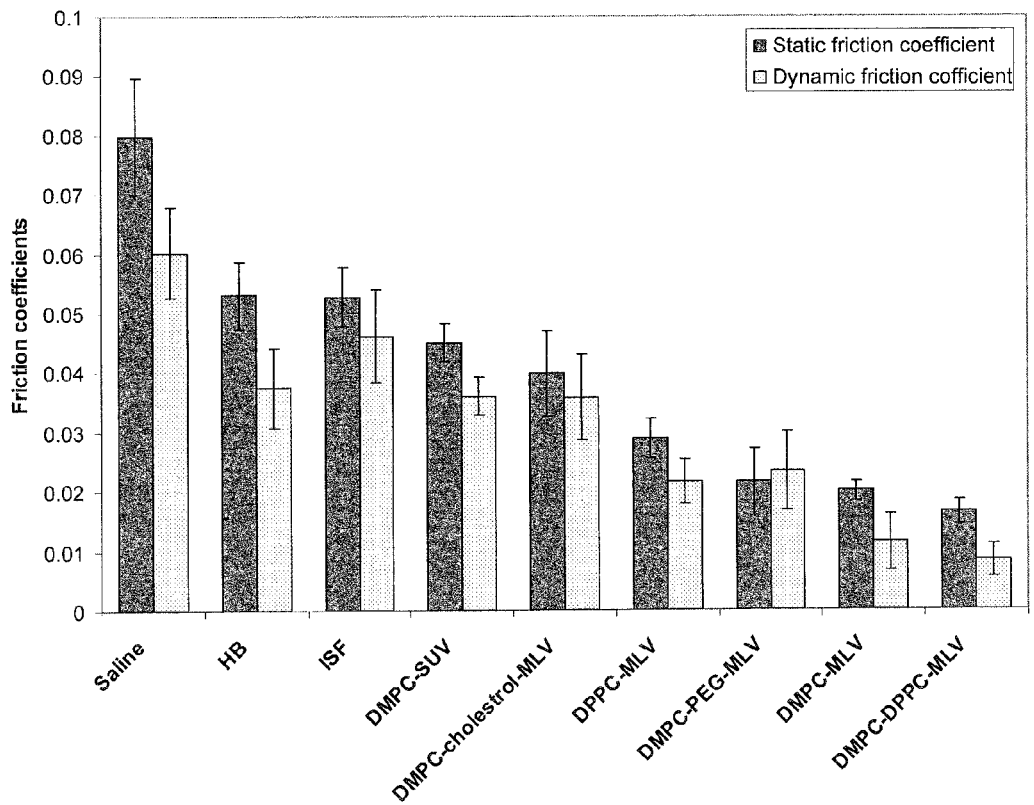
FIG. 1 is a bar graph showing the friction coefficients (static and dynamic) obtained for various lubricating media, including inflamed synovial fluid (ISF); histidine buffer (HB, 5 mM), dispersions comprising multilamellar vesicles (MLV, carried in 5 mM HB, the lipids being at a concentration range of between 35-140 mM) with the phospholipid being DMPC, MLV comprising DMPC, or DMPC-cholesterol, or mixture of DMPC and $^{2000}$PEG-DSPE DMPC or a mixture of DMPC and DPPC, or small unilamellar vesicles (SUV) comprising DMPC. All measurements were performed at 37° C. under contact pressure of 2.4 MPa (30N load) and sliding velocity of 1 mm/s. Saline was used as a control.

The present invention is based on results, inter alia, making use of a human cartilage-on-cartilage setup (Merkher, Y. et al.[40]) where the following were determined (i) friction coefficient measurements, (ii) wear of human articular cartilage (iii) cartilage morphological studies based on SEM, (iv) cartilage quantitative phospholipid and phosphatidylcholine (PC) determinations, and (v) physicochemical characteristics of different PC-based liposomes, which demonstrated the potential of large (diameter greater than 0.3 μm) multilamellar vesicles, such as DMPC-MLV and of DMPC/DPPC-MLV (0.6/1.0 mole ratio), dispersed in low ionic-strength histidine buffer (HB), as effective cartilage lubricants and wear reducers at temperature slightly above (e.g. about 1° C., 2° C., 3° C., 5° C., 8° C., 11° C. and at times up to about 15° C.) the Solid Order to Liquid Disorder (SO-to-LD) phase transition temperature.

Initially, the lubricating efficacy of multilamellar liposomes composed of various PCs, with two hydrocarbon chains from 14 to 22 carbons, fully saturated or with varying degrees of un-saturation, was compared. $C_{12}$-$C_{16}$ hydrocarbon chains where shown to be of preferred length.

Then, using the most effective single-component lubricant, DMPC, the effects of liposome size, lamellarity, and of incorporating either cholesterol, mPEG-DSPE or an additional PL into the lipidic bilayer of DMPC liposomes was investigated. These studies showed that MLV, such as DMPC-MLV or DMPC/DPPC-MLV (0.8-3.5 μm in diameter), when used as lubricants at temperature slightly above the SO-to-LD phase transition temperature, were most effective. This was confirmed by the performance of DMPC/DPPC-MLV at 37° C., which is slightly above the range of its SO-to-LD phase transition temperature, i.e., $T_m$=~34° C., in comparison to its performance at 24° C. (SO phase).

The results presented herein below further show the following:

DMPC, which was identified as one preferred component of the liposomal biolubricant composition (when used alone or in combination with DPPC has saturated, medium-length acyl chains (14 carbons), having a $T_m$ slightly lower than the physiological temperature ($T_m$=23.2° C. for DMPC-MLV and $T_m$=~34° C. for DMPC/DPPC [0.6/1.0 mole/mole] used), thus both PC compositions providing liposomes which are in the LD phase at 37° C. (see Table in Materials and Methods below). When in the LD phase, PC polar headgroup is highly hydrated (~9.7 water molecules per DMPC or DPPC headgroup, in comparison to <4.3 water molecules per headgroup when below the $T_m$ in the SO phase)[53];

The adiabatic compressibility data presented herein below demonstrate the differences between PC in the solid-ordered (SO) phase (low K values) and the LD phase (higher K values) and the superiority of the LD phase. Partial adiabatic lipid bilayer compressibility (K), which correlates well with the thermotropic behavior[54] and was found to reflect the level of hydration, physical state and the volume of cavities (free volume) in the lipid bilayer[45]. Bound water molecules, which interact with the PC headgroup, are suggested to affect the total volume of cavities in the bilayer, thus affecting intermolecular interactions, as well as the adiabatic compressibility. Specifically, both DOPC and DMPC are in the LD phase (above their $T_m$, Table 1 below) at (24° C. as well as at 37° C. However, the lubrication ability of DMPC liposomes was substantially superior to that of DOPC. Without being bound by theory, it is believed that the difference in behavior between DMPC and DOPC resides in the fact that under physiological conditions, i.e. at a temperature of between 36° C. and 43° C. DMPC is only slightly above the $T_m$. Moreover, the temperature in synovial joints of the hand can be as low as ~28 C. Under such conditions DMPC is also slightly above the $T_m$. In addition, DMPC is the PC with the shortest acyl chains capable of forming stable liposomes, thus composing the mechanically "softest" bilayer of all other single-component PC bilayers exemplified herein[44].

The lubrication ability of MLV composed of DMPC/DPPC (0.6:1.0 mole/mole) mixture having good miscibility and nearly ideal mixing properties, and a combined SO-to-LD phase transition temperature of ~34° C. The DMPC/DPPC-MLV showed high lubricating efficacy at 37° C. (static and dynamic friction coefficients of 0.017 and 0.0083, respectively) but not at 24° C. (0.042 and 0.021, respectively), compared with DPPC-MLV alone ($T_m$ of 41.4° C.) which were inferior at 37° C. (0.029 and 0.022, for the static and dynamic friction coefficients, respectively);

The more efficient lubrication achieved by using liposomes with $T_m$ only slightly below physiological temperature.

The protection of cartilage from wear using MLV composed of DMPC/DPPC, where a mixture of DMPC/DPPC added to ISF, substantially reduced the wear in comparison to ISF alone and ISF with an addition of HA; this protection effect being significantly higher than the other exemplified membrane, in particular that composed of DPPC alone.

Figure 5:
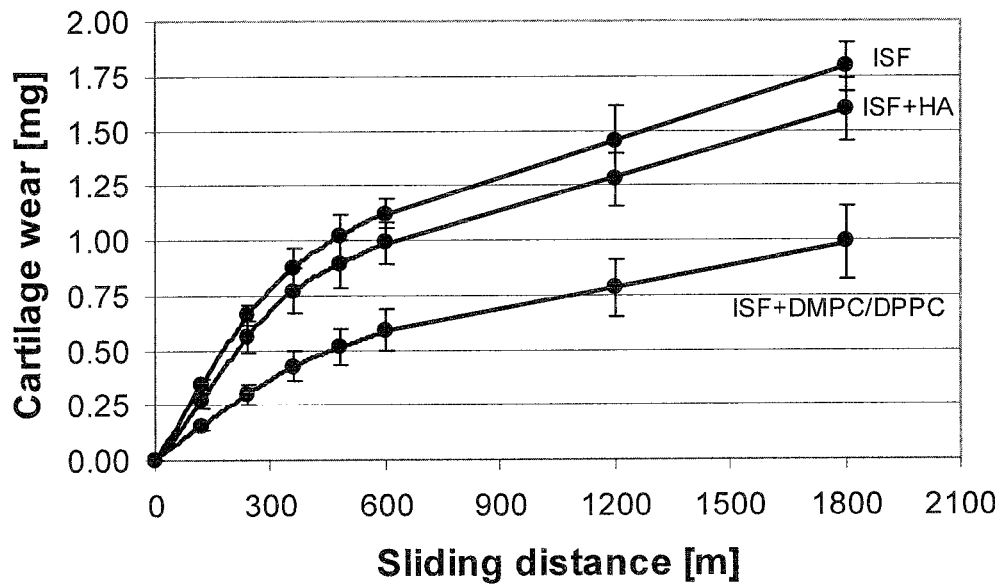
FIG. 5 is a graph showing cartilage wear as a function of sliding distance in the presence of ISF, ISF+HA and ISF+DMPC/DPPC.
Figure 6:
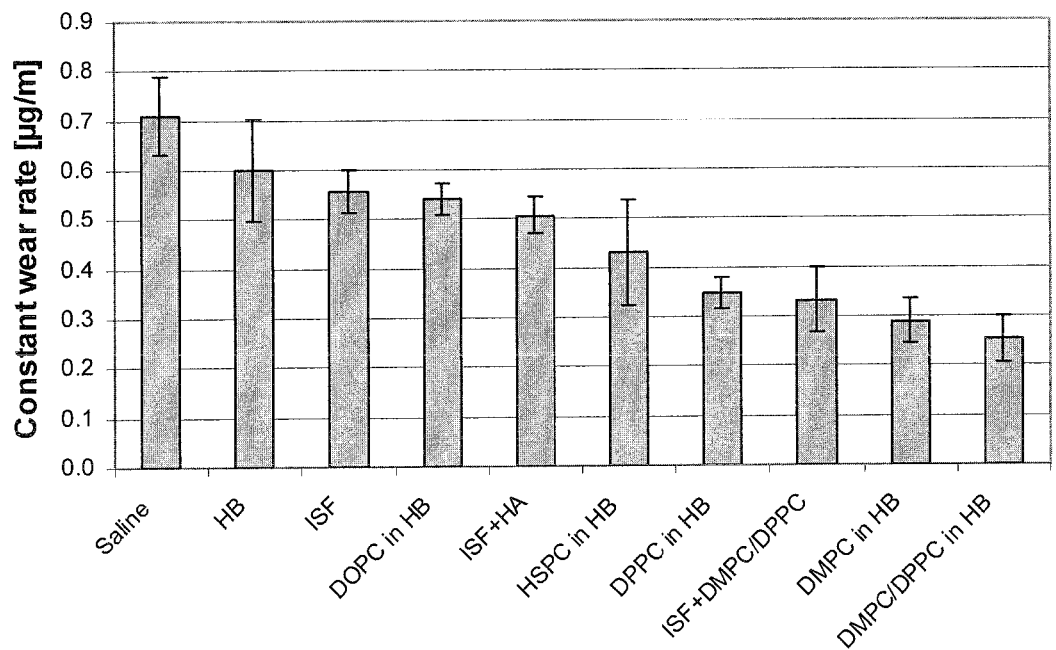
FIG. 6 is a bar graph showing the constant wear rates obtained with different lubricating fluids (Saline, HB or HA) and phospholipids (DOPC, HSPC, DPPC, DMPC/DPPC or DMPC), used as liposome additives, following a run-in period.
Figure 7:
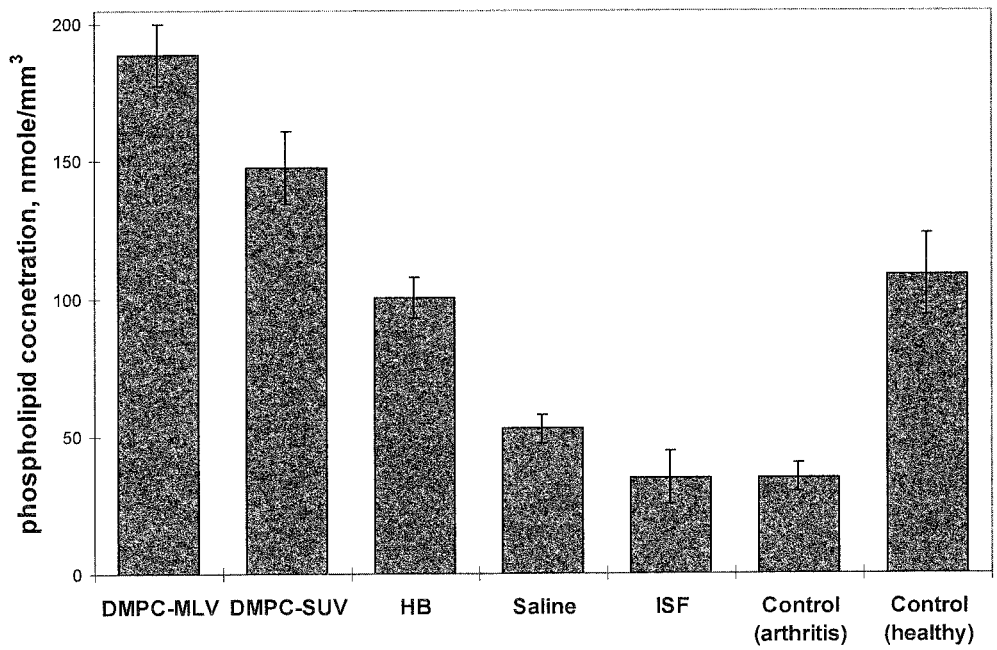
FIG. 7 is a graph showing the effect of the various lubricants and media on total phospholipid concentration, in cartilage specimens from healthy individuals after being subjected to similar friction tests in the presence of the different lubricants. The controls were not subjected to friction tests.
Figure 8:
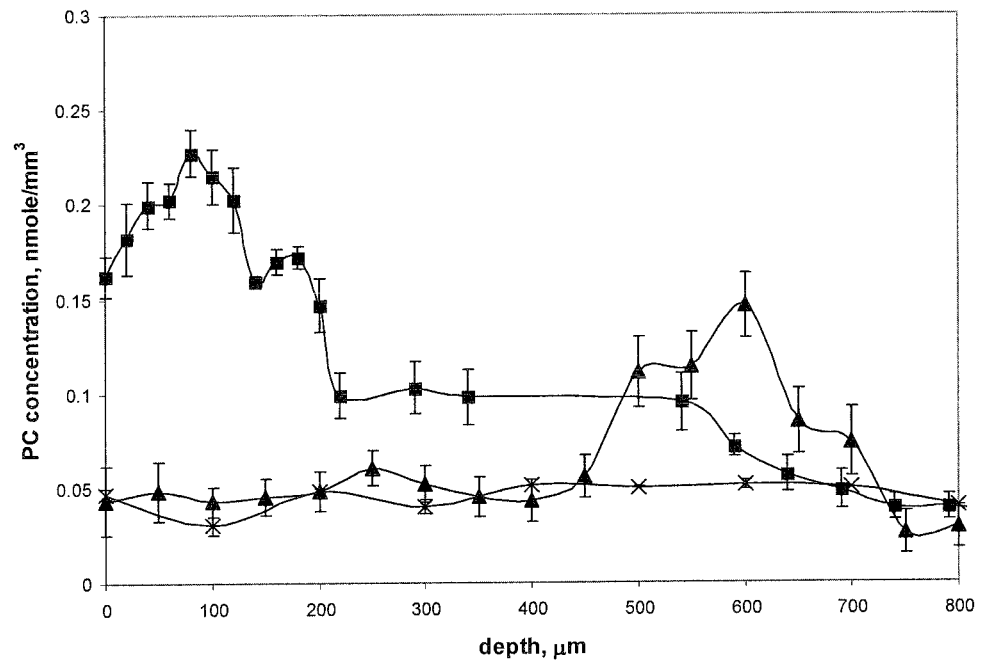
FIG. 8 is a graph showing PC concentration as a function of vertical depth into cartilage where cartilage specimens were subjected to similar friction tests in the presence of: DMPC-MLV (0.8-3.5 μm in diameter) 141 mM in 5 mM HB (■); DMPC-SUV (~100 nm in diameter) 141 mM in 5 mM HB (▲); or HB alone 5 mM (x); sliced into discs and tested for their DMPC concentration as a function of cartilage depth.

The "softness" and hydration level of DMPC-MLV and the impact of changes in these features on cartilage lubrication. The first modification in formulation included introduction of ~33 mole % cholesterol into liposome membranes. As shown below, this resulted in a physical transition from the LD phase to the liquid-ordered (LO) phase[34]. Such a change is known to "dry" the lipid bilayer[56], and is also reflected in a reduction in the adiabatic compressibility and therefore in bilayer softness. Therefore, lubricating cartilage with DMPC/cholesterol-MLV was substantially inferior to lubricating of cartilage with DMPC-MLV (FIG. 1). In another modification 5 mole % of the lipopolymer mPEG-DSPE into the lipid bilayer of DMPC-MLV was introduced. The PEG moieties, extending 4-10 nm from the liposome surface (depending on the polymer chain state, being either in a mushroom or brush configuration[39]), and are highly flexible and highly hydrated (3 to 4 water molecules per ethylene oxide group)[45]. However, addition of mPEG-DSPE to DMPC liposomes did not improve lubrication (FIG. 1), which seemed to be contradictory to the role of hydration in lubrication. This may be explained by the fact that the PEG moiety although highly polar is nonionic and therefore its hydration differs from that of the hydration of ionic the PC headgroup[45]. It must be noted, that these grafted PEG moieties may still be beneficial in vivo as they can protect the liposomes from interacting with macromolecules of interstitial fluid[34], similarly to the cartilage-protecting behavior of HA[22];

Friction coefficients obtained by different media (saline, ISF, and low ionic strength HB) demonstrated that HB was superior to saline and to ISF (FIGS. 1, 2, 5-7). Furthermore, the total PL concentration of cartilage specimens lubricated with HB was nearly twice that of cartilage lubricated with ISF and substantially higher than that of cartilage lubricated with saline (FIG. 7). Suggesting that HB may better retain naturally-occurring cartilage SAPLs, thereby improving lubrication. The superiority of HB over saline (FIG. 1) can also be explained by its lower ionic strength, which induces a less compact PL packing in the lipid bilayer, thus enabling rapid bilayer recovery after frictional events[34, 57]. This further supports the importance of bilayer softness as a major contributor to effective lubrication. From the above, it became apparent that HB is an effective and supportive medium for liposomes as lubricants;

Large multilamellar DMPC-MLV were found to be superior to small unilamellar liposomes (<100 nm). Without being limited by theory as it is not required for the establishment of the invention, it is believed that this superiority stems from the way the former are retained near the cartilage surface, as demonstrated by the PC distribution along cartilage depth (FIG. 8), due to the large size of MLV (0.8-3.5 μm in diameter). Maroudas et al. reported the presence of 100-nm gaps between collagen fibers in cartilage[50]. Stockwell and Barnett[51] and Barnett and Palfrey[52] state that these fibers act as barriers against penetration of large particles into the cartilage, reporting that small silver proteinate particles penetrated deeper than large particles into cartilage. The results presented herein show that smaller DMPC-SUV penetrated deeply into cartilage, while DMPC-MLV remained near the surface (FIG. 8). This is in agreement with the similarity of friction levels obtained from cartilage lubricated with DMPC-SUV in HB and of cartilage lubricated with HB alone (FIG. 1), as DMPC-SUV penetrate deeply into the cartilage the effect of lubrication is primarily of the media (i.e. HB).

Figures 9A, 9B:
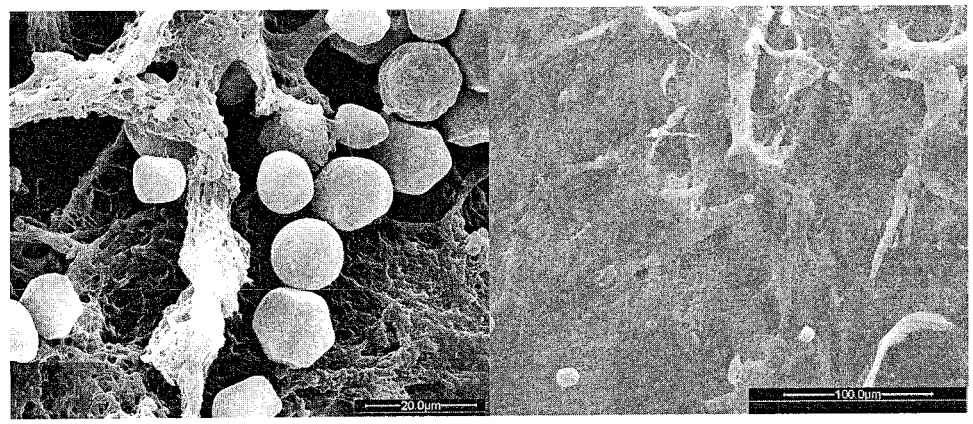
FIGS. 9A-9F are scanning electron microscope (SEM) micrographs of cartilage specimens in the presence and absence of lubricating media and friction tests. SEM micrographs of control specimens, in the absence of friction test.
Figures 9C, 9D:
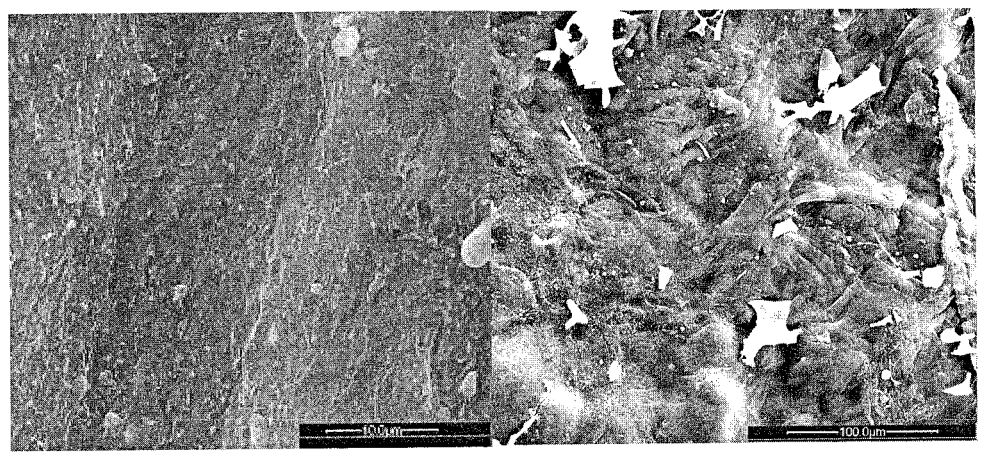
Figures 9E, 9F:
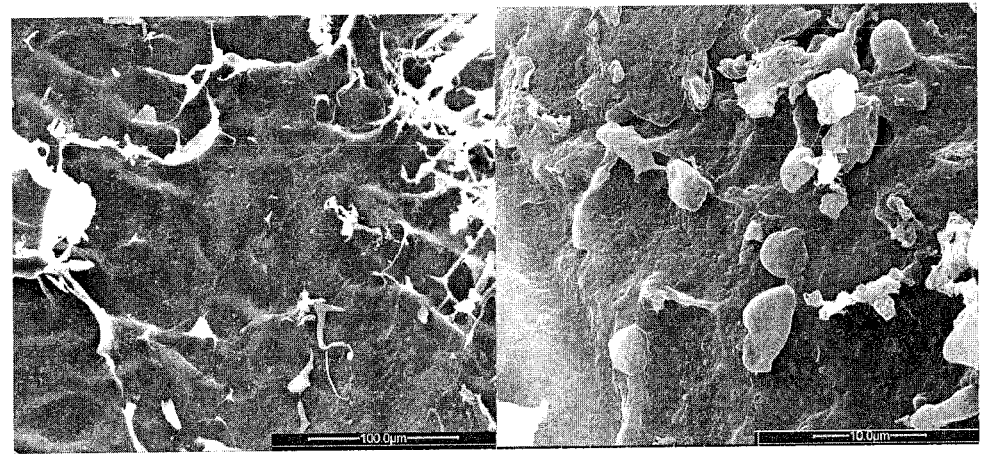

SEM morphological studies, in which naturally-occurring globular structures, in the size range of DMPC-MLV, seemed to be present on the surface of healthy non-lubricated cartilage prior to conducting friction tests (FIG. 9A), and absent after friction tests of healthy cartilage lubricated with saline or ISF (FIGS. 9C and 9D, respectively). Cartilage specimens lubricated with DMPC-MLV seemed to have globular lipidic structures on their surface, after conducting friction tests (FIG. 9F).

In light of these results, it has been envisaged that phospholipids (PL) selected from glycerophospholipids (GPL) and sphingolipids (SPL), are potential substituents for the naturally-occurring lipidic globular structures, being capable of reducing friction and protecting against cartilage wear.

Further, it has been envisaged that when present near cartilage surface liposomes comprising GPL, SPL or their combination as the liposome forming phospholipids act as a reservoir for replenishing a protective lipid bilayer coating the cartilage surface, thus assisting in preservation of naturally-occurring PL, as indicated by the higher total PL level in cartilage lubricated with DMPC-MLV in comparison to cartilage lubricated with other lubricants and media (FIG. 82).

In accordance with some embodiments of the invention, the GPL is carrying a phosphocholine headgroup (phosphatidylcholine, PC-based lipid) or a phosphoglycerol headgroup (phosphatidylglycerol, PG-based lipid), and the SPL is a ceramide (N-acyl sphingosine carrying a phosphocholine headgroup, also referred to as N-acyl sphigosyl-phosphocholine (SM-based lipid).

As appreciated by those versed in lipid based technologies, PCs and SMs are zwitterionic phospholipids with the cationic choline and anionic diester phosphate moieties (constituting the phopshocholine head group) remain fully ionized over a broad pH range with no net charge (zeta potential=0 mV)[34]. The PG is negatively charged over broad pH range as evident from it negative zeta potential. The hydrophobic part of the PC and PG includes 2 hydrocarbon (e.g. acyls and alkyls) chains. The SM also has two hydrophobic hydrocarbon chains of which one is the chain of the sphingoid base itself and the other is N-acyl chain. PC, SM and PG in which the hydrocarbon chains is above 12 carbon atoms are all cylinder like in shape as their packing parameter is in the range of 0.74-1.0. They form lipid bilayers which above the SO to LD phase transition become highly hydrated and vesiculate to form lipid vesicles (liposomes)[34, 35]. The PC and PG liposome bilayer can be either in a solid ordered (SO) phase (previously referred to as gel or solid phase), or in a liquid disordered (LD) phase (previously referred to as liquid crystalline or fluid phase)[34]. The transformation between the SO to LD phases involves an endothermic, first order phase transition referred to as the main phase transition. $T_m$ is the temperature in which the maximum change in the heat capacity change during the SO to LD phase transition occurs. $T_m$ and the temperature range of the SO to LD phase transition of PCs depend, inter alia, on PC hydrocarbon chain composition. In the LD phase (but not in the SO phase), the charged phopshocholine and phosphoglycerol head group are highly hydrated.

It is further noted that PGs and SM have $T_m$ that are similar to that of the corresponding PC (the same length of substituting hydrocarbon chain(s)). For instance, the $T_m$ of DMPG is identical to that of DMPC, namely, 23° C., and that of DPPG or N-palmitoyl SM is identical to that of DPPC, namely, 41.4° C. Thus, while the following examples make use of PC-based lipids, the PL in accordance with the invention may also be a PG- or SM-based lipid.

In accordance with the invention, a mixture of two or more PLs (e.g. two different PCs, a PC with PG, two different PGs, two SM, a PC or PG with SM, etc) may be used, as long as the mixture formed is in a LD state and the lipid headgroups are highly hydrated, when in situ (either at the articular region of a healthy or a dysfunctioning joint).

Having considered the above, the inventors have developed liposomal systems for joint lubrication, which are chemically stable, oxidative-damage-resistant and free of HA.

Thus, in accordance with an aspect of the invention, the use of a liposome comprising at least one PL selected from glycerophospholipid (GPL) or sphingolipid (SPL), for joint lubrication is provided.

By another aspect of the invention, there is provided the use of a liposome comprising at least one PL selected from glycerophospholipid (GPL) or sphingolipid (SPL), for the preparation of a pharmaceutical composition for joint lubrication.

The liposomes in accordance with both aspects being characterized in that they comprise one or more membranes with at least one phospholipid (PL) of the group consisting of a glycerophospholipid (GPL) having two, being the same or different, $C_{12}$-$C_{16}$ hydrocarbon chains and a sphingolipid (SPL) having a $C_{12}$-$C_{18}$ hydrocarbon chain. The phase transition temperature in which solid ordered (SO) to liquid disordered (LD) phase transition occurs is within a temperature range of about 20° C. to about 39° C. The liposomes are used to lubricate joints that have a joint temperature that is somewhat higher than the phase transition temperature. Accordingly the liposomes are in an LD phase within the joint. The fact that the joint temperature is typically only slightly (e.g. within the range of about 1° C. to about 15° C., as detailed above) above the phase transition temperature seems to be of importance for efficient lubrication.

In one preferred embodiment said $C_{12}$-$C_{16}$ or $C_{12}$-$C_{18}$ hydrophobic chains are saturated.

It is noted that the above conditions are cumulative, namely, the selection of PL (either a single PL or a combination of PL with additional PLs) contained in the liposome is so that the liposome will have SO-LD phase transition temperature between about 20° C. to about 39° C.

In accordance with additional embodiments of the invention, the liposomal systems making use the said GPL or SPL further encompass one or more of the following, all of which require to exhibit a liposomal system having a phase transition temperature as defined herein:

The GPL or SPL have alkyl, alkenyl or acyl $C_{12}$ to $C_{16}$ hydrocarbon chain. In the case of GPL, the two chains may be the same or different.

One particular embodiment concerns the use of liposomes having GPL or SPL with at least one $C_{14}$ acyl chain.

Another particular embodiment concerns the use of a GPL having $C_{14}$ and $C_{16}$ acyl chains.

Another particular embodiment concerns the use of liposomes having SPL with a $C_{16}$ acyl chain.

Another particular embodiment concerns the use of a combination of any of the above liposomes.

Some GPL or SPL have a ionic headgroup and, according to embodiments of the invention, this headgroup is highly ionized at a wide range of pH. A wide range may be defined by a pH between 3 and 14.

The GPL as well as the SPL are highly hydrated, namely, the number of water molecules per lipid headgroup is at least about 6; 7 or at times at least 8 water molecules that are complexed to the ionized head group of the GPL or SPL.

The GPL or SPL are capable of forming MLV (as well as the other type of liposomes mentioned above), preferably MLV having a mean diameter above 0.3 μm. According to one embodiment, the MLV are defined by a mean diameter in the range of between 0.3 μm and 5 μm. According to another embodiment, the MLV are defined by a mean diameter in the range of between 0.8 μm and 3.5 μm.

As cholesterol was found to reduce lubrication properties of the MLV being formed from GPL, SPL or their combinations, as defined herein, the MLV or the other types of liposomes that may be used in accordance with the invention should not include in their bilayers a membrane active sterol, such as cholesterol. A membrane active sterol is defined as affecting short- and long-range lipid order within membranes, minimizing volume, and decreasing membrane permeability. Specifically, the sterol should possess 1), a flat, fused ring system, 2), a hydroxyl or other small polar group at position 3, 3), a "cholesterol-like" tail, and 4), a small area per molecule (<40 Å$^2$ when assembled at the air/water interface at a surface pressure of 12 mN/m).

It is to be noted that the compositions of the invention preferably do not contain propylene glycol.

It should further be noted that the compositions of the invention preferably do not contain dextran.

A particular group of GPLs encompassed by one or more of the above embodiments comprise a GPL carrying a phosphocholine headgroup (PC or SM-based lipids). One preferred PC in accordance with the invention is dimyristoylphosphatidylcholine (DMPC).

Non-limiting examples of PC-based lipids which may be used in accordance with the invention comprise 1,2-dipalmitoyl-sn-glycero-3-phosphocoline (DPPC, $T_m$ 41.4° C.); 1,2-dipentadecanoyl-sn-glycero-3-phosphocoline (C15, $T_m$ 33.0° C.), albeit, these two being suitable only when combined with one or more other lipids so as to form a liposomal system having a phase transition temperature as defined herein. SPL which may be in accordance with the invention comprise a sphingomyelin (SM) carrying a phosphocholine headgroup, and non-limiting examples include N-palmitoyl SM $T_m$ 41.0° C. and 1,2-dimyristoyl-sn-glycero-3-PC. $T_m$ values of various PC-based lipids may be found in "Thermotropic Phase Transitions of Pure Lipids in Model Membranes and Their Modifications by Membrane Proteins", John R. Silvius, *Lipid-Protein Interactions*, John Wiley & Sons, Inc., New York, 1982, and also in the Lipid Thermotropic Phase Transition Data Base—LIPIDAT, and in Marsh (1990)[36].

It is noted that in accordance with the invention the MLV liposomes (or the other liposomes useful according to the invention) have an offset temperature (upper limit) of the SO to LD phase transition which is not higher than 15° C. from the temperature in situ, i.e. in the joint, within the range of about 20° C. to about 39° C. In accordance with the invention the MLV liposomes are formed from GPL, SPL or their combination, and the SO to LD phase transition temperature described above thus concerns MLV liposomes which are formed from GPL, SPL and combinations thereof, thus providing a liposome in which the PLs or their mixture are in LD phase.

A particular embodiment in accordance with the invention concerns the use of DMPC-MLV or DMPC/DPPC-MLV for the preparation of a replacement of naturally-occurring cartilage PL, namely as a cartilage lubricant and wear reducer. These MLV have major practical advantages as well. They can be prepared simply and at low cost. DMPC and DPPC are both resistant to oxidative damage and stable for long periods of time. Furthermore, these PCs are already approved for human use. According to one embodiment, when using a mixture of DMPC and DPPC, the mole ratio between DMPC and DPPC depends on the temperature of the joint to be treated and is designed such that the $T_m$ of the combination provides MLV in LD phase. One example of a suitable ratio is about 0.6/1.0 which provides MLV in LD phase at a joint temperature between 35° C. to 39° C.

In accordance with an additional aspect of the invention there is provided a method for lubricating a joint of a mammal, the method comprises administering into a cavity of said joint containing synovial fluid an amount of liposomes effective to yield a lubricating effect.

It is noted that the temperature of joints in patients afflicted with reduced joint lubrication or with joint wear, such as osteoarthritis varies as the disease proceeds [Hollander, J. L.; Moore, R., Studies in osteoarthritis using Intra-Articular Temperature Response to Injection of Hydrocortisone. *Ann. Rheum. Dis.* 1956, 15, (4), 320-326]. In fact, this temperature change was used as a clinical tool for assessing osteoarthritis inflammation [Thomas, D.; Ansell, B. M.; Smith, D. S.; Isaacs, R. J., Knee Joint Temperature Measurement using a Differential Thermistor Thermometer. *Rheumatology* 1980, 19, (1), 8-13]. In hand joints of osteoarthritis patients temperature was shown to vary from ~28 to ~33° C. [Varju, G.; Pieper, C. F.; Renner, J. B.; Kraus, V. B., Assessment of hand osteoarthritis: correlation between thermographic and radiographic methods. *Rheumatology* 2004, 43, 915-919], while the temperature of healthy Temporomandibular joint (TMJ) varies from ~35 to 37° C. [Akerman, S.; Kopp, S., Intra-articular and skin surface temperature of human temporomandibular joint. *Scand. J. Dent. Res.* 1987, 95, (6), 493-498].

Thus, in accordance with the invention it is essential and in fact a pre-requisite that the GPL or the mixture thereof with additional PLs, be in a LD phase, in situ, at the joint region to be lubricated therewith.

The method of the invention may be used to treat, alleviate, retard, prevent, manage or cure any articular disorder or symptoms arising there from which is associated with joint dysfunction. For the purposes of this disclosure the term "articular disorder" shall be held to mean any affliction (congenital, autoimmune or otherwise), injury or disease of the articular region which causes degeneration, pain, reduction in mobility, inflammation or physiological disruption and dysfunction of joints. The disorder may be associated with reduced joint secretion and lubrication as well as from complications of knee and hip replacement.

The joint in accordance with the invention may be any one of the knee, hip, ankle, shoulder, elbow, tarsal, carpal, interphalangeal and intervertebral.

Specific articular disorders include, but are not limited to, deficiencies of joint secretion and/or lubrication arising from arthritis, including conditions of joint erosion in rheumatoid arthritis, osteoarthritis, osteoarthritis in rheumatoid arthritis patients, traumatic joint injury (including sports injury), locked joint (such as in temporomandibular joint (TMJ)), status post arthrocentesis, arthroscopic surgery, open joint surgery, joint (e.g. knee or hip replacement) in mammals, preferably humans. A preferred disorder to be treated or prevented by the method of the invention is osteoarthritis.

The method of the present invention could be used as a prophylactic measure to prevent future damage or degeneration. For example, the PL based MLV liposomes could be administered intra-articularly to athletes intermittently throughout their career to minimize the risk of stress related injury or cartilage degeneration.

The method of the present invention may be used exclusive of, or as an adjunct to, anti-inflammatory agents, analgesic agents, muscle relaxants, anti-depressants, or agents that promote joint lubrication commonly used to treat disorders associated with joint stiffness, such as arthritis. A combined therapeutic approach is beneficial in reducing side effects associated with agents, such as non-steroidal, anti-inflammatory drugs (NSAIDs), commonly used to prevent, manage, or treat disorders such as osteoarthritis associated with reduced joint lubrication. In addition to enhancing safety, a combined therapeutic approach may also be advantageous in increasing efficacy of treatment.

The administration of the liposomes into an articular cavity of a patient may be by a method chosen from the group consisting of intra-articular injection, arthroscopic administration or surgical administration.

The invention also provides, in accordance with yet another aspect of the invention, a pharmaceutical composition for joint lubrication comprising a physiologically acceptable carrier and liposomes comprising at least one PL selected from GPL or SPL as defined herein.

In accordance with one embodiment, the physiologically acceptable carrier is hyaluronic acid (HA) or histidine buffer (HB). The composition may also include polymers such as those described by Klein et. al.[31].

The composition according to the invention is preferably in a form suitable for administration by a route selected from intra-articular injection, arthroscopic administration or surgical administration.

The amount of liposomes in the composition will vary depending on the liposome's PL composition, the disease, its severity and treatment regimen, as well a on the age, weight, etc., of the mammal to be treated. The amount for purposes herein is determined by such considerations as may be known in the art. The amount must be effective to achieve an improvement in the lubrication of the treated joint, namely, to reduce friction between the cartilages forming the joint, the improvement may be exhibited by clinical tests as well as by an improvement in the well-being of the subject undergoing said treatment (e.g. reduced pain in the afflicted joint, improvement in mobility). The effective amount is typically determined in appropriately designed clinical trials (dose range studies) and the person versed in the art will know how to properly conduct such trials in order to determine the effective amount.

Throughout the description and claims of this specification, the singular forms "a" "an" and "the" include plural references unless the context clearly dictates otherwise. Thus, for example, a reference to "a PL" is a reference to one or more PLs and "a liposome" refers to one or more liposomes. Throughout the description and claims of this specification, the plural forms of words include singular references as well, unless the context clearly dictates otherwise.

Yet, throughout the description and claims of this specification, the words "comprise" and "contain" and variations of the words, for example "comprising" and "comprises", mean "including but not limited to", and are not intended to (and do not) exclude other moieties, additives, components, integers or steps.

The invention will now be described by way of non-limiting examples.

DESCRIPTION OF NON-LIMITING EXAMPLES

Example 1

Materials and Methods

Lipids:

Lipids used in this study and their sources are described in Table 1; all are >98% pure. Table 1 also presents the solid-ordered (SO) to liquid-disordered (LD) phase transition temperatures, $T_m$, of phospholipid bilayers,[34-36] as well as the bilayer state at 37° C.

TABLE 1

| | phase transition temperatures | | |
|---|---|---|---|
| Lipid | Chemical name (source) | Phase at 37° C. | Phase transition temperature $(T_m)$, ° C. |
| HSPC | hydrogenated soybean phosphatidylcholine (Lipoid, Ludwigshafen, Germany) | SO | 52.5 |
| DPPC | 1,2-dipalmitoyl-sn-glycero-3-phosphocholine (Avanti, Alabaster, AL, USA) | SO | 41.4 |
| DMPC | 1,2-dimyristoyl-sn-glycero-3-phosphocholine (Lipoid or Avanti) | LD | 23.2 |
| DOPC | 1,2-dioleoyl-sn-glycero-3-phosphocholine (Lipoid or Avanti) | LD | −21 |
| Mixture of DMPC/DPPC (0.6/0.1) | | LD | 34 |

Water: Water was purified using a WaterPro PS HPLC/Ultrafilter Hybrid system (Labconco, Kansas City, Mo.), providing pyrogen-free water with low levels of total carbons and inorganic ions (18.2 MΩ).

Reagents: All other reagents used are of analytical grade or better.

Liposomes: Multilamellar liposomes (MLV) were prepared by dissolving the desired lipids in tert-butanol, followed by lyophilization to form a dry "cake". This was hydrated in low ionic strength (5 mM) histidine buffer (HB) pH 6.7, at a temperature at least 5° C. above the $T_m$.[34] When desired, MLV were downsized to form small unilamellar vesicles (<100 nm, SUV) by stepwise extrusion through polycarbonate membranes (GE-Osmonics, Minnetonka, Minn.), starting with a 400-nm and ending with a 50-nm-pore-size membrane, using a 10-mL extrusion system (Northern Lipids, Vancouver, Canada) heated at least 5° C. above the $T_m$.[37]

Figure 3:
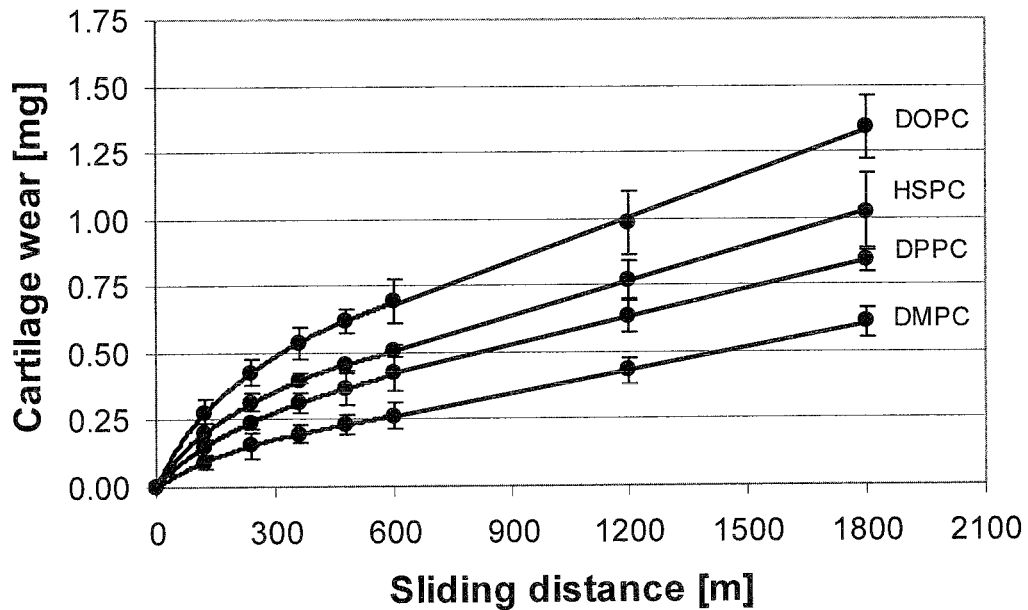
FIG. 3 is a graph showing cartilage wear as a function of sliding distance in the presence of DOPC, HSPC, DPPC and DMPC, all dispersed in HB.

Initial screening of cartilage lubricants was performed with MLV of different PC compositions—DMPC, DPPC, HSPC, DBPC, DOPC and POPC (for abbreviations see Table 1). In this screening it was found that DMPC liposomes acted as the best friction reducers (FIGS. 1 and 3). Therefore, DMPC-based liposomes were further investigated comparing liposomes composed of either DMPC alone, of different sizes and lamellarities, or of a DMPC/DPPC mixture (0.6:1.0 mole ratio), or of DMPC combined with cholesterol (2:1 mole ratio), or of DMPC combined with the lipopolymer mPEG-DSPE (95:5 mole ratio). The mPEG-DSPE used consists of a 2000 Dalton polyethylene glycol attached to the primary amino group of distearoyl phosphatidylethanolamine.

Liposome characterization: Liposomes were characterized for:

(i) phospholipid (PL) concentration, using the modified Bartlett assay[37, 38];

(ii) size distribution, for liposomes under 1 μm by dynamic light scattering using an ALV-NIBS High Performance Particle Sizer (Langen, Germany) at a scattering angle of 173°; and for liposomes above 400 nm by light diffraction using a Beckman Coulter LS Particle Size Analyzer 13-320 (Fullerton, Calif.), equipped with polarization intensity differential scattering (PIDS) to provide a dynamic detection range from 40 nm to 2000 μm;

(iii) partial specific adiabatic compressibility, by calculation from the density of the liposome dispersion (using a DMA 5000 density meter, Anton Paar, Graz, Austria) and the velocity of an 5 MHz ultrasonic wave traveling through it (using a UCC-12 ultrasonic velocimeter, NDT Instruments, Jerusalem, Israel), as described by Garbuzenko et al.[39]; and (iv) structure, using scanning electron microscopy (SEM).

Cartilage: Articular cartilage from healthy or osteoarthritis humans (aged 65 to 86 years) was obtained from femoral head fracture operations or total hip replacements. Tissue was classified as normal or pathological according to the visual diagnosis. For wear rate determination, only femoral heads with normal tissue were selected. Specimens were frozen at −20° C. until sample preparation in order to keep the mechanical properties close to those of live tissue. Pairs of cylindrical plugs, having 4 mm and 8 mm in diameter, each pair from the same region of the joint, were prepared. These cylindrical plugs, consisting of about 2 mm thick cartilage on top of about 8 mm long bone, were removed from the femoral head using a cork borer. The plugs were glued to holders through the bone part, using cyanoacrylate-based adhesive glue, leaving the cartilage projecting out of the holders. Thereafter, these plugs were refrozen at −20° C. until tested. Cartilage with completely intact and smooth surface was used. Friction and wear testing: Liposomes covering a wide range of sizes and concentrations, dispersed in HB, were screened as potential lubricants to reduce friction and wear between two discs of human cartilage at 24° C. and 37° C. Friction measurements were carried out with a cartilage-on-cartilage setup (Merkher, Y.; Sivan, S.; Etsion, I.; Maroudas, A.; Halperin, G.; Yosef, A., A rational human joint friction test using a human cartilage-on-cartilage arrangement. *Tribol. Lett.* 2006, 22, 29-36, the content of which is incorporated herein by reference in its entirety), using two discs of cartilage immersed in a liposomal dispersion in HB, or as controls, in HB alone, or in physiological saline (0.9% w/v; pH 5.0; Teva Medical, Israel), or in inflamed synovial fluid (ISF) obtained from osteoarthritis patients. These discs were subjected to relative sliding over a wide range of loads (1 to 30 N), equivalent to physiological pressures in joints (0.08 to 2.4 MPa). Various sliding velocities (0.5 to 2 mm/s) and dwell times (5 to 300 s) were used to simulate, together with various loads, a range of physiological movements.

For the a qualitative evaluation of wear, the effect of friction tests on the concentration of total PL in cartilage, and on the structure of the cartilage surface was determined.

PL extraction and quantification: Total PL were extracted from cartilage specimens before and after lubrication tests, using the Bligh and Dyer extraction procedure[41, 42]. For this, cartilage specimens were incubated in a chloroform-methanol solution (1:1 v/v) for 1 h at 37° C. Water was added to a final chloroform-water-methanol ratio of 1:1:1, the solution was Vortexed for 1 min and then centrifuged, using a desk centrifuge, to form two phases. The chloroform-rich lower phase, containing the PL, was collected, dried under vacuum (Concentrator 5301, Eppendorf), and the residual (containing lipids) was re-dissolved in a small volume of chloroform-methanol solution (2:1 v/v) and then loaded onto low-phosphorus silica gel TLC glass plates (Uniplate—Silica Gel G, Analtech, Newark, Del.). A chloroform-methanol-water (65:25:4 v/v/v) solvent system was used for TLC[41]. Commercial markers of sphingomyelin, PC and PE were also loaded on the plates for spot identification. Lipid spots were detected after spraying the dried TLC plates with a UV-detectable primulin (Sigma) solution (1 mL of 0.1% w/v primulin in water, added to 100 mL acetone-water, 4:1 v/v). Each PL spot was scraped from the TLC plate, and its PL content was quantified by the modified Bartlett procedure.[37, 38]

PL concentration was also quantified as a function of cartilage depth. For this, cartilage specimens were sectioned by microtome into slices 20 or 50 μm thick, from the cartilage surface inwards, parallel to the face of the cartilage. PL concentration of each slice was quantified, after PL were extracted as mentioned above, by the modified Bartlett procedure[37, 38].

Wear determination test: For the wear test, human inflamed synovial fluid (ISF) was retrieved from several inflamed joints. It was pooled in order to obtain a large quantity of uniform ISF for different tests with and without liposome additives. Commercially available HA (10 mg/mL, pH 6.7, of rooster comb MW 1-4×10$^6$, catalog no. H5388 Sigma, USA) which is used for intra-articular administration into osteoarthritis joints, was tested as another additive to ISF in order to investigate its effect on articular cartilage wear in comparison to liposome additives.

The reciprocating sliding amplitude was set to 1 mm, assuring full contact between the two cartilage samples during the wear test. Each test was carried out for 7.5 hours with an average reciprocating velocity of 4 m/min. This resulted in a maximum of 450,000 reciprocating cycles for each test, which amounts to a total sliding distance of 1800 m. Normal load of 60 N corresponding to contact pressure of 4.8 MPa, which is well in the range of physiological pressures in joints, was used. In order to compensate for any possible loss of cartilage components (which can occur, for example, from loose ends at the circumferential cylindrical cut surface of the plugs during agitation in the lubricating fluid), experiments with identical test conditions but with no load and no contact between the cartilage specimens were also conducted. The actual wear was calculated by subtracting the results at no load from these obtained when load was applied.

A pair of frozen specimens was thawed, and the upper and lower specimens were fixed to a wear test loading mechanism and a bath, respectively. A volume of 1.5 ml of the lubricating fluid was placed in the bath and the reciprocating sliding motion started after applying a normal load (compensation at 0 N, and wear test at 60 N).

As more than 95% of the glycosaminoglycans (GAGs) in articular cartilage is sulphated (mainly chondroitin sulfate and keratan sulfate)[61], analyzing for GAG content[62] in the aqueous cartilage medium containing the wear particles (particles of the wear debris released from both cartilage surfaces into the lubricating fluid) was used to assess the wear of the two cartilage specimens.

Cartilage structure: Cartilage structure was examined by SEM. Specimens were preserved by rapid cooling in liquid nitrogen and kept under vacuum (~15 mbar) for 48 h to remove excess water. Next, specimens were mounted on stubs and sputter-coated with gold in a Polaron E5100 Sputter Coater (Watford, England). The specimens were examined using an FEI Quanta 200 scanning electron microscopy system (Polaron) using an accelerating voltage of 30 kV.

Results

Figure 2:
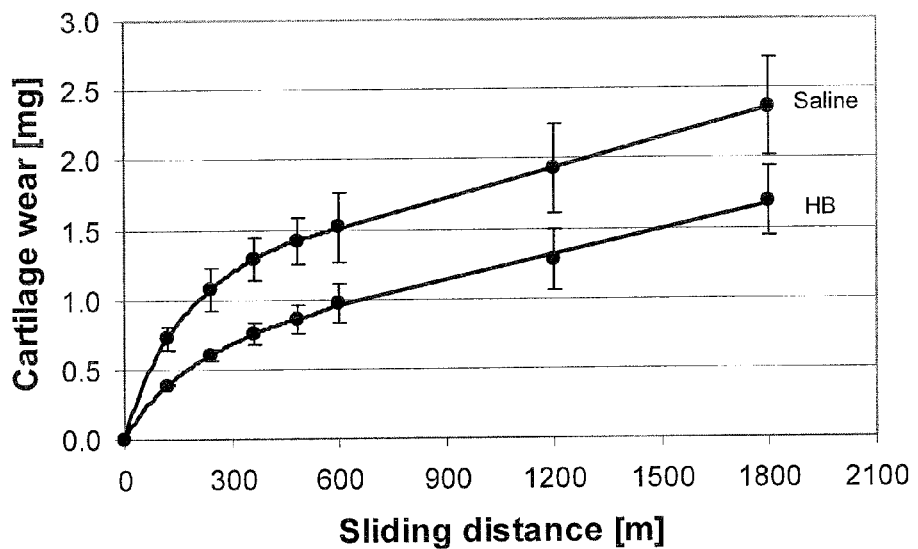
FIG. 2 is a graph showing cartilage wear as a function of sliding distance in the presence of two different potential carrier media HB and saline, the cartilage wear being measured by analyzing the glycosamineglycan (GAG) content weight in the debris present in the aqueous medium of the cartilage as a result of wearing.

Liposome carrier: it was found that the lubrication efficiency of HB is better than that of saline, or of ISF (FIG. 1). Furthermore, liposomes dispersed in HB were better lubricants than liposomes dispersed in saline (FIG. 2). Thus, in the following, liposome additives to be screened for their cartilage-lubricating abilities were all dispersed in HB.

The surface-active phospholipids (SAPL) tested were phosphatidylcholines (PCs), which are also naturally present in cartilage and synovial fluid.

Screening liposomes for cartilage lubrication and wear reduction, involved comparison of a cartilage wear as well as static and dynamic friction coefficients obtained with MLV composed of various single-component PCs. The exemplified PCs differ in their acyl chains, which determine the basic characteristics of the liposomes, especially the $T_m$ and physical state.

Screening MLV (0.8 to 3.5 μm in diameter) composed of different PCs (DMPC, DPPC, HSPC, DBPC, DOPC and POPC) revealed that both at 24° C. and 37° C., DMPC was the best-performing cartilage lubricant. This was confirmed in FIG. 3 which show the amount of cartilage wear found in the presence of DOPC, HSPC, DPPC and DMPC, all dispersed in HB as a function of sliding distance. Similar behavior of wear to that in the presence of media alone (FIG. 2), but with lower wear values, was shown for all liposome types. Comparing cartilage wear in the presence of different liposome additive showed that DMPC ($T_m$=23.2° C.) is superior lubricant additive, both in lower wear values during the run-in period and in lower constant wear rate thereafter. Similar results were found for the friction tests described in FIG. 1.

Figure 4:
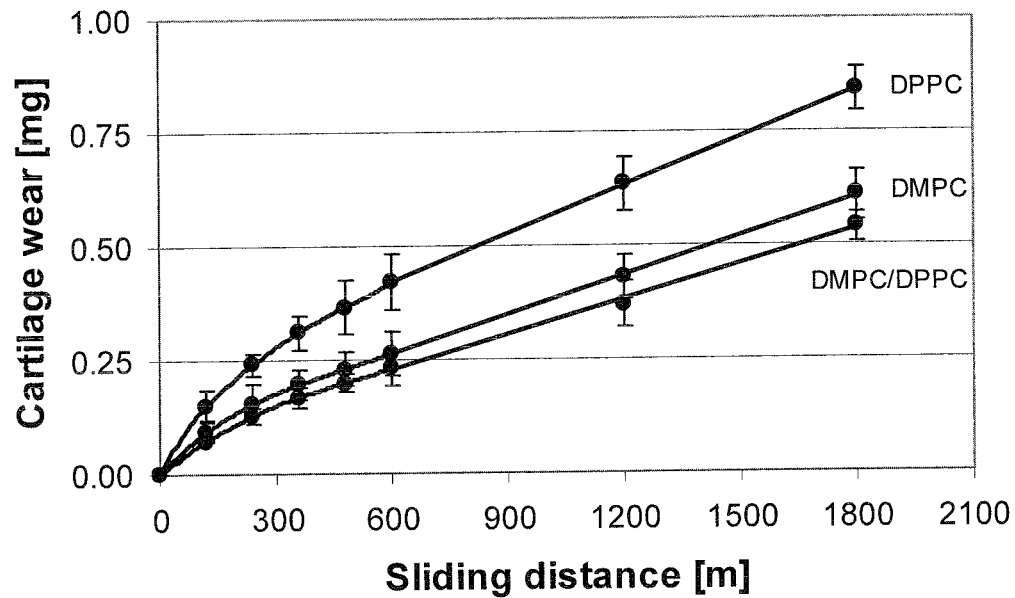
FIG. 4 is a graph showing cartilage wear as a function of sliding distance in the presence of DPPC, DMPC and a mixture of DMPC/DPPC, all dispersed in HB.

In addition, FIG. 4 shows the amount of cartilage wear found in the presence of DPPC, DMPC and a mixture of DMPC/DPPC, all dispersed in HB, as a function of sliding distance. Cartilage wear in the presence of the DMPC/DPPC mixture (0.6/1.0 mole/mole $T_m$=34° C.) and DMPC ($T_m$=23.2) were similar and both were significantly lower than that exhibited in the presence of DPPC MLV ($T_m$ 41.4° C.) liposomes alone.

Using liposomes composed of a mixture of close to ideally miscible PC's (no phase separation) may enable fitting their $T_m$ to suit a wide range of temperatures. For example, the ratio of DMPC/DPPC can be adjusted, so that phase transition would take place at all physiological temperatures occurring in different conditions of osteoarthritis. ISF, ISF+DMPC/DPPC, ISF+HA: In order to determine whether an addition of liposomes in ISF can reduce wear, comparative tests were performed in the presence of ISF alone and ISF+DMPC/DPPC. Of all the liposomes tested earlier, the mixture of DMPC/DPPC was chosen as it was found to be the most efficient lubricant additive (see FIGS. 3 and 4). ISF+DMPC/DPPC (150 mM) was prepared by adding a mixture of DMPC/DPPC in HB with a concentration of 300 mM to ISF with a ratio of 1:1.

One of the treatments commonly used in osteoarthritis patients is intra-articular administration of HA into inflamed joints. The effectiveness of this treatment is still a controversial issue and therefore it is of interest to study the effect of ISF+HA on cartilage wear reduction in comparison with that of ISF alone and ISF+DMPC/DPPC. A common symptom in osteoarthritis patients is excessive synovial fluid production. Therefore, aspiration of the joint is usually performed before the HA injection. The excessive fluid production, which continues after the HA injection, constantly changes the ratio of HA and ISF in the injected inflamed joint. Since the actual ratio of HA and ISF as a function of time is not known, a fixed typical ratio of 1:1 was selected for the current tests in accordance with the same ratio of ISF and DMPC/DPPC. This ratio is probably higher than the one in actual injected osteoarthritis joints and therefore its effect on wear reduction may be considered as an upper limit.

FIG. 5 shows the amount of cartilage wear found in the presence of ISF, ISF+HA and ISF+DMPC/DPPC as a function of sliding distance. Similar behavior of wear to that in the presence of media alone and other liposome based lubricants was shown, where a relatively short run-in period was followed by a long constant wear rate period. Comparing cartilage wear in the presence of the different lubricants shows that although the addition of HA to ISF induces less wear than ISF alone, the addition of DMPC/DPPC mixture to ISF is much more effective in terms of reducing cartilage wear.

A summary of the constant wear rates following the run-in period, that were obtained with all the different lubricating fluids and additives is presented in FIG. 6. As can be seen, the constant wear rate of cartilage in the presence of HB is lower in comparison with saline and therefore HB was selected as the preferred carrying media for all the tested liposome types. Screening the different liposomes shows that the lowest constant wear rate is achieved in the presence of the mixture of DMPC/DPPC. Moreover, adding DMPC/DPPC to ISF reduces the constant wear rate by ~40% compared with ISF alone, while adding HA to ISF reduces the constant wear rate only by ~10%. Based on these results it was suggested that intra-articular injections of DMPC/DPPC may be used to improve cartilage lubrication in osteoarthritis patients.

Friction and wear in cartilage lubricated with several DMPC-based liposomes: Investigating the effect of liposome size and lamellarity, the lubricating efficacy of multilamellar DMPC liposomes (DMPC-MLV) was compared to that of <100-nm unilamellar DMPC liposomes (DMPC-SUV). In addition, the efficacy as cartilage lubricants of DMPC-MLV enriched with lipids which are non-liposome-forming, although are common liposome components, such as cholesterol or mPEG-DSPE, was studied. Cholesterol, having a packing parameter of ~1.2[39], was added at ~33 mole % to form DMPC/cholesterol-MLV, thus causing the transformation of the lipid bilayer from the solid-ordered (SO, if PL are below the $T_m$) or liquid-disordered (LD, if PL are above $T_m$) phase to a new physical phase termed liquid-ordered (LO)[43, 44]. Thereby, it was possible to compare the effect of liposomes at the three different bilayer phases LD, SO and LO on lubrication. Another component added to DMPC-MLV was the lipopolymer mPEG-DSPE, having a relatively low packing parameter of ~0.5[39], which introduces a highly-hydrated extended steric barrier that surrounds the liposome[39, 45]. mPEG-DSPE was added at 5 mole % to form DMPC/mPEG-DSPE-MLV.

The static and dynamic friction coefficients of DMPC-MLV in HB (0.020 and 0.011, respectively) were lower than those obtained with DMPC/cholesterol-MLV in HB (0.040 and 0.036, respectively) or DMPC/mPEG-DSPE-MLV in H13 (0.022 and 0.023, respectively), as shown in FIG. 1, and were similar to the low friction coefficients which exist in healthy synovial joints[46]. Furthermore, the static and dynamic friction coefficients of cartilage lubricated with DMPC-MLV were lower than those of cartilage lubricated with DMPC-SUV (0.045 and 0.036, respectively) which were only slightly lower than those of HB alone (0.053 and 0.037, respectively), FIG. 1.

Statistical evaluation, by Student's t test, indicated the superiority of DMPC-MLV over the other liposome formulations tested at this assay and media (p<0.008).

Compressibility of the lipid bilayer: The partial specific adiabatic compressibility, K, is a measure of both the physical phase of the lipid bilayer (SO, LD or LO) and its hydration state, which is postulated herein to have an important contribution to the liposomes' efficacy as friction and wear reducers[45] Values of K for DMPC, DPPC and hydrogenated soy phosphatidylcholine (HSPC) determined at 37° C. were 50.7, 31.2 and 33.3×10$^{-6}$ mL/(g-atm), respectively. A similar profile, with somewhat lower values of K, 46.4, 28.0 and 30.3×10$^{-6}$ mL/(g-atm), was found at 24° C. for DMPC, DPPC and HSPC, respectively. These K values reflect the higher phase transition temperatures, $T_m$, of DPPC and HSPC (41.4° C., 52.5° C.) than that of DMPC (23.2° C.) and thus the superiority of liposomes having a membrane having a phase transition in the range defined in the present invention ($T_m$ between 20° C. to 39° C. inclusive). In DMPC/cholesterol liposomes (2:1 mole ratio) K is reduced to 42.2 and 45.5×10$^{-6}$ mL/(g-atm) at 24° C. and 37° C., respectively. Introducing 5 mole % mPEG-DSPE into HSPC liposomes (T, 53° C.)[39] raised compressibility to 32.8 and 35.5×10$^{-6}$ mL/(g-atm) at 24° C. and 37° C., respectively. While in HSPC/cholesterol liposomes (2:1 mole ratio) K is reduced to 30.0 and 33.6×10$^{-6}$ mL/(g-atm) at 24° C. and 37° C.

Without being bound by theory, the above results suggest that the physical phase of the MLV bilayers are important for cartilage biolubrication, and that the optimal conditions for lubrication are being at the LD phase, not to far above the SO-to-LD phase transition temperature ($T_m$). To further test this hypothesis the inventors tested MLV composed of 0.6/1.0 (mole/mole) DMPC/DPPC. This composition was selected so as to enable the formation of a liposome having a $T_m$ of ~34° C.[47] (being possible due to the nearly ideal mixing of these two PCs). These MLV were studied at 24° C. and 37° C. The results clearly support the above hypothesis, as they show (FIG. 1) that DMPC/DPPC-MLV are the most effective lubricants at 37° C. (static and dynamic friction coefficient of 0.017 and 0.0083, respectively) but not at 24° C. (static and dynamic friction coefficient of 0.042 and 0.021, respectively). Furthermore DMPC/DPPC-MLV were superior to DPPC-MLV ($T_m$=41.3) alone, which are inferior at 37° C. (static and dynamic friction coefficient of 0.029 and 0.022, respectively).

PL levels in lubricated cartilage specimens: The total PL (which includes naturally-occurring SAPLs and PLs from liposomes) levels of healthy cartilage specimens (thickness ~1200 μm), before and after being subjected to friction tests, in the presence of different lubricants and media, was measured. It can be seen (FIG. 8) that the total PL concentration in cartilage lubricated with DMPC-MLV is the highest among all specimens tested. The PL concentration of cartilage obtained from healthy subjects and lubricated with FIB is higher than that of similar cartilage lubricated with saline or ISF, the latter (ISF), has similar PL levels to that of cartilage obtained from osteoarthritis patients.

Effect of Liposome Size and Lamellarity on their Penetration into Cartilage: PC concentration, as a function of cartilage depth (0-800 μm, in 20-50-μm increments), was measured after friction tests for specimens lubricated with DMPC-MLV and DMPC-SUV, both dispersed in HB, and for specimens lubricated with HB alone (control). Among these specimens, cartilage lubricated with DMPC-MLV had the highest PC concentration near the cartilage surface (FIG. 8). PC concentration reached a maximum at a depth of ~100 μm, below which, it decreased. On the other hand, in cartilage lubricated with DMPC-SUV the highest PC concentration occurred deep (~600 μm) inside the cartilage, while at the surface PC concentration was similar to that of the control (cartilage lubricated with HB).

Cartilage morphology: SEM was used to study cartilage surface morphology and wear[28]. In FIG. 9 we present SEM images of cartilage specimens subjected to different treatments. The two control specimens (FIGS. 9A and 9B) were not subjected to friction tests, whereas all other specimens (FIGS. 9C-9F) of cartilage were obtained from healthy people and subjected to identical friction tests in the presence of different lubricants. FIG. 9A shows healthy cartilage, where naturally-occurring globular lipidic structures are dispersed on its porous surface, as previously shown on the surface of rat cartilage by Ohno et al.[28, 48]. On the other hand, the surface of osteoarthritic cartilage lacks these structures (FIG. 9B), as does friction-tested healthy cartilage lubricated with saline (FIG. 9C) or ISF (FIG. 9D), indicating poor protection against wear by these lubricants. On the surface of cartilage lubricated with DMPC-SUV (FIG. 9E), very few lipidic structures can be noticed after friction testing. With DMPC-MLV (FIG. 9F), large lipidic structures, resembling those on healthy cartilage, are present after friction testing.

Example 2

Toxicity Study

The present example was conducted to assess local reactions (histopathology of fermorotibial joint) at different times post intraarticular injection of DMPC-based MLV composed of either DMPC alone or of a DMPC/DPPC mixture (0.6:1.0 mole ratio) in Sprague Dawley (SD) rats.

Materials & Methods

Animals: 46 male SD rats aged 9 weeks old (purchased from Harlan Laboratories Ltd. Israel) were randomly assigned to 5 groups, 9 animals per group. The rats were maintained at Assaf Harofe Medical Center animal facility. The rats treated by intraarticular injection according to an initial assignment (Table 2, Group composition, treatments and Identification of animals). Rat in general good condition were included. All rats were treated on Day 1, and one group was treated again on Day 14. Both knees were treated; each knee was injected with 100 μL of one of the test liposomes or control substance. Cages were marked with a clear label and permanent marker. The rats were marked on their tail.

TABLE 2

Group composition, treatments and Identification of animals

| Animal No. | Cage No. | Tail No. | Left knee | Right Knee |
|---|---|---|---|---|
| 1, 10, 19, 28, 37 | 1, 4, 7, 10, 13 | 1 | HB | DMPC |
| 2, 11, 20, 29, 38 | | 2 | HB | DMPC |
| 3, 12, 21, 30, 39 | | | | DMPC |
| 4, 13, 22, 31, 40 | 2, 5, 8, 11, 14 | 1 | Physiological saline | DMPC + DPPC |
| 5, 14, 23, 32, 41 | | 2 | Physiological saline | DMPC + DPPC |
| 6, 15, 24, 33, 42 | | | HB | DMPC + DPPC |
| 7, 16, 25, 34, 43 | 3, 6, 9, 12 15 | 1 | DMPC | DMPC |
| 8, 17, 26, 35, 44 | 15 | 2 | DMPC + DPPC | DMPC |
| 9, 18, 27, 36, 45, 46 | | 4 | DMPC + DPPC DMPC + DPPC | DMPC DMPC |

*Physiological saline: 0.9% NaCl

Test compositions: Liposomal DMPC and DMPC+DPPC were prepared as described above (the liposomes being dispersed in HB) and stored in 4° C. till one hour before the application. The last hour before the application they were left in room temperature. The concentrations of the liposomes were for DPPC 100.6 mM and for DMPC+DPPC 92.0 mM.

The physiological solution that was used is 0/9% w/v sodium chloride (purchased from B. Braun batch No. 7281C12 exp. 08.2010).

Treatment procedure: Before the toxicity test the rats were anesthetized by inhalation of Isoflurane (Abbot Laboratories). The rats knees were shaved by an electric machine, skin sprayed with 70% alcohol. A 1 mL syringes were used with a replaceable 27 gauge needles. The needles were chanced after each injection. 100 μL was injected each time. At the end of the study, rats were euthanized by exposure to carbon dioxide.

Table 3 summarizes the weights and treatment of each rat.

TABLE 3

Table of weights and treatments

| Rat No. | Cage No. | Tail No. | Left knee | Right Knee | Initial Weight | $2^{nd}$ weight | Final Weight | $2^{nd}$ treatment | Eutanization |
|---|---|---|---|---|---|---|---|---|---|
| 1 | 1 | 1 | HB | DMPC | 298 | | 303 | No | day (19/12) |
| 2 | 1 | 2 | HB | DMPC | 310 | | 316 | | |
| 3 | 1 | 3 | Physiological saline | DMPC | 300 | | 295 | | |
| 4 | 2 | 1 | Physiological saline | DMPC + DPPC | 310 | | 318 | | |
| 5 | 2 | 2 | Physiological saline | DMPC + DPPC | 298 | | 285 | | |
| 6 | 2 | | HB | DMPC + DPPC | 290 | | 292 | | |
| 7 | 3 | 1 | DMPC + DPPC | DMPC | 285 | | 277 | | |
| 8 | 3 | 2 | DMPC + DPPC | DMPC | 290 | | 295 | | |
| 9 | 3 | | DMPC + DPPC | DMPC | 290 | | 286 | | |
| 10 | 4 | 1 | HB | DMPC | 302 | | 307 | No | 4 days (22/12) |
| 11 | 4 | 2 | HB | DMPC | 303 | | 324 | | |
| 12 | 4 | | Physiological saline | DMPC | 298 | | 317 | | |
| 13 | 5 | 1 | Physiological saline | DMPC + DPPC | 315 | | 330 | | |
| 14 | 5 | 2 | Physiological saline | DMPC + DPPC | 314 | | 330 | | |
| 15 | 5 | | HB | DMPC + DPPC | 282 | | 292 | | |
| 16 | 6 | 1 | DMPC + DPPC | DMPC | 280 | | 280 | | |
| 17 | 6 | 2 | DMPC + DPPC | DMPC | 305 | | 305 | | |
| 18 | 6 | | DMPC + DPPC | DMPC | 298 | | 298 | | |
| 19 | 7 | 1 | HB | DMPC | 312 | | 312 | No | fortnight (1/1) |
| 20 | 7 | 2 | HB | DMPC | 299 | | 299 | | |
| 21 | 7 | | Physiological saline | DMPC | 318 | | 318 | | |
| 22 | 8 | 1 | Physiological saline | DMPC + DPPC | 303 | | 303 | | |
| 23 | 8 | 2 | Physiological saline | DMPC + DPPC | 300 | | 300 | | |
| 24 | 8 | | HB | DMPC + DPPC | 300 | | 300 | | |
| 25 | 9 | 1 | DMPC + DPPC | DMPC | 300 | | 300 | | |
| 26 | 9 | 2 | DMPC + DPPC | DMPC | 321 | | 321 | | |
| 27 | 9 | | DMPC + DPPC | DMPC | 300 | | 300 | | |
| 28 | 10 | 1 | HB | DMPC | 313 | | 405 | No | 4 weeks (15/1) |
| 29 | 10 | 2 | HB | DMPC | 310 | | 409 | | |
| 30 | 10 | | Physiological saline | DMPC | 298 | | 318 | | |
| 31 | 11 | 1 | Physiological saline | DMPC + DPPC | 289 | | 356 | | |
| 32 | 11 | 2 | Physiological saline | DMPC + DPPC | 298 | | 364 | | |
| 33 | 11 | | HB | DMPC + DPPC | 308 | | 404 | | |
| 34 | 12 | 1 | DMPC + DPPC | DMPC | 290 | | 355 | | |
| 35 | 12 | 2 | DMPC + DPPC | DMPC | 312 | | 420 | | |
| 36 | 12 | | DMPC + DPPC | DMPC | 315 | | 389 | | |
| 37 | 13 | 1 | HB | DMPC | 306 | 361 | 400 | fortnight 1/1 | 4 weeks (15/1) |
| 38 | 13 | 2 | HB | DMPC | 298 | 342 | 374 | | |
| 39 | 13 | | Physiological saline | DMPC | 300 | 338 | 359 | | |
| 40 | 14 | 1 | Physiological saline | DMPC + DPPC | 301 | 351 | 383 | | |
| 41 | 14 | 2 | Physiological saline | DMPC + DPPC | 298 | 341 | 355 | | |
| 42 | 14 | | HB | DMPC + DPPC | 300 | 338 | 368 | | |
| 43 | 15 | 1 | DMPC + DPPC | DMPC | 306 | 348 | 384 | | |
| 44 | 15 | 2 | DMPC + DPPC | DMPC | 291 | 336 | 337 | | |
| 45 | 15 | | DMPC + DPPC | DMPC | 298 | 338 | 384 | | |
| 46 | 15 | 4 | DMPC + DPPC | DMPC | 298 | 351 | 352 | | |

Clinical Evaluation: The animal technician held physical observations on the rats throughout the study for monitoring prominent change in their conditions such as drastic weight loss, wounds or deaths. All rats were weighted before the applications and after euthanization.

Necropsy: All rats were subjected to a full detailed necropsy and gross pathological examination at the end of the study period following euthanasia. At necropsy, all rats were thoroughly examined for any abnormality or gross pathological changes in tissues and/or organs. Samples of all knees were sent to slides preparation at Patho-Lab Ltd. Ness Ziona. Tissue fixation was obtained in formaldehyde (Bio-Lab Ltd.).

Results

No pathological changes were observed in any of the rats during necropsy procedure.

Histopathological data indicated that the general reaction to the test compositions, following one and four days from the administration consisted of:
Synovial cytoplasmic vacuolation—ranged from minimal to mild;
Subsynovial vacuolated histiocytic cell accumulation—ranged from minimal to mild;
Articular cavity—exudate (fibrillar amorphous material, histiocyes and polymorphonuclear cells)—ranged from minimal to mild;

The nature and severity of changes were relatively comparable in the DMPC and DMPC+DPPC treated rats.

No lesions were noted in the rats examined 2 and 4 weeks after administration, suggesting complete recovery.

Thus, that the pathology results show that both liposomal preparations (DMPC and DMPC:DPPC (6:1)) could be considered as a safe intra-articular treatment.

REFERENCES

1. Alexander, C. J. Idiopathic osteoarthritis: time to change paradigms? *Skeletal Radiol.* 33, 321-324 (2004).
2. Corti, M. C. & Rigon, C. Epidemiology of osteoarthritis: prevalence, risk factors and functional impact. *Aging Clin. Exp. Res.* 15, 359-363 (2003).
3. Bullough, P. G. & Vigorita, V. J. Orthopaedic Pathology, Edn. 3rd. (Mosby-Wolfe, Baltimore; 1997).

4. Koopman, W. J. & Moreland, L. W. Arthritis and Allied Conditions: A Textbook of Rheumatology, Vol. 1-2, Edn. 15th. (Lippincott Williams & Wilkins, Philadelphia; 2005).
5. Sokoloff, L. The biology of degenerative joint disease. *Acta Rhumatol Belg.* 1, 155-156 (1977).
6. Conaghan, P. G., Vanharanta, H. & Dieppe, P. A. Is progressive osteoarthritis an atheromatous vascular disease? *Ann. Rheum. Dis.* 64, 1539-1541 (2005).
7. Neame, R. & Doherty, M. Osteoarthritis update. *Clin. Med.* 5, 207-210 (2005).
8. Imhof, H. et al. Subchondral bone and cartilage disease: a rediscovered functional unit. *Invest. Radial.* 35, 581-588 (2000).
9. Lajeunesse, D. & Reboul, P. Subchondral bone in osteoarthritis: a biologic link with articular cartilage leading to abnormal remodeling. *Curr. Opin. Rheumatol.* 15, 628-633 (2003).
10. Radin, E. L. Who gets osteoarthritis and why? *J. Rheumatol. Suppl.* 70, 10-15 (2004).
11. Grainger, R. & Cicuttini, F. M. Medical management of osteoarthritis of the knee and hip joints. *Med. J. Aust.* 180, 232-236 (2004).
12. Swaim, D. A., Hendren, R. B., Radin, E. L., Sotman, S. L. & Duda, B. A. The lubricating activity of synovial fluid glycoproteins. *Arthritis Rheum,* 24, 22-30 (1981).
13. Swarm, D. A. & Mintz, G. The isolation and properties of a second glycoprotein (LGP-II) from the articular lubricating fraction from bovine synovial fluid. *Biochem. J.* 179, 465-471 (1979).
14. Swami, D. A., Slayter, H. S. & Silver, F. H. The molecular structure of lubricating glycoprotein-1, the boundary lubricant for articular cartilage. *J. Biol. Chem.* 256, 5921-5925 (1981).
15. Nitzan, D. W., Kreiner, B. & Zeltser, R. TMJ lubrication system: its effect on the joint function, dysfunction, and treatment approach. *Compend. Contin. Educ. Dent.* 25, 437-444 (2004).
16. Yui, N., Okano, T. & Sakurai, Y. Inflammation responsive degradation of crosslinked hyaluronic acid gels. *J. Control. Release* 22, 105-116 (1992).
17. Hills, B. A. & Butler, B. D. Surfactants identified in synovial fluid and their ability to act as boundary lubricants. *Ann. Rheum. Dis.* 43, 641-648 (1984),
18. Sarma, A. V., Powell, G. L. & LaBerge, M. Phospholipid composition of articular cartilage boundary lubricant. *J. Orthop. Res.* 19, 671-676 (2001).
19. Schwarz, I. M. & Hills, B. A. Surface-active phospholipid as the lubricating component of lubricin. *Br. J. Rheumatol.* 37, 21-26 (1998).
20. Hills, B. A. & Monds, M. K. Enzymatic identification of the load-bearing boundary lubricant in the joint. *Br. J. Rheumatol.* 37, 137-142 (1998).
21. Ogston, A. G. & Stanier, J. E. Physiological function of hyaluronic acid in synovial fluid; viscous, elastic, and lubricant properties. *J. Physiol. (Cambridge)* 119, 244-252 (1953).
22. Benz, M., Chen, N. & Israelachvili, J. Lubrication and wear properties of grafted polyelectrolytes, hyaluronan and hylan, measured in the surface forces apparatus. *J. Biomed. Mater. Res. A.* 71, 6-15 (2004).
23. Rhee, D. K. et al, The secreted glycoprotein lubricin protects cartilage surfaces and inhibits synovial cell overgrowth. *J. Clin. Invest.* 115, 622-631 (2005).
24. Swann, D. A., Bloch, K. J., Swindell, D. & Shore, E. The lubricating activity of human synovial fluids. *Arthritis Rheum.* 27, 552-556 (1984).
25. Pickard, J. E., Fisher, J., Ingham, E. & Egan, J. Investigation into the effects of proteins and lipids on the frictional properties of articular cartilage. *Biomaterials* 19, 1807-1812 (1998).
26. Vecchio, P., Thomas, R. & Hills, B. A. Surfactant treatment for osteoarthritis. *Rheumatology (Oxford)* 38, 1020-1021 (1999).
27. Gudimelta, O. A., Crawford, R. & Hills, B. A. Consilidation responses of delipidized cartilage. *Clin. Biomech.* 19, 534-542 (2004).
28. Watanabe, M. et al. Ultrastructural study of upper surface layer in rat articular cartilage by "in vivo cryotechnique" combined with various treatments. *Med. Elect. Microsc.* 33, 16-24 (2000).
29. Kawano, T. et al. Mechanical effects of the intraarticular administration of high molecular weight hyaluronic acid plus phospholipid on synovial joint lubrication and prevention of articular cartilage degeneration in experimental osteoarthritis. *Arthritis Rheum.* 48, 1923-1929 (2003).
30. Forsey, R. W. et al. The effect of hyaluronic acid and phospholipid based lubricants on friction within a human cartilage damage model. *Biomaterials* 27, 4581-4590 (2006).
31. Klein, J. Molecular mechanisms of synovial joint lubrication. *J. Proc. Inst. Mech Eng., Part J: J. Eng. Tribology* 220, 691-710 (2006).
32. Briscoe, W. H. et al. Boundary lubrication under water. *Nature* 444, 191-194 (2006).
33. Raviv, U. et al. Lubrication by charged polymers. *Nature* 425, 163-165 (2003).
34. Barenholz, Y. & Cevc, G. Structure and properties of membranes in Physical Chemistry of Biological Surfaces. (Marcel Dekker, New York; 2000).
35. Israelachvili, J., Intermolecular and surface Forces, $2^{nd}$ edition, Academic Pres, London (1992)
36. Marsh, D. CRC Handbook of Lipid Bilayers. (CRC Press, Boca Raton, Fla.; 1990).
37. Barenholz, Y. & Amselem, S. Quality control assays in the development and clinical use of liposome-based formulations in Liposome Technology, Edn. 2nd, (CRC, Boca Raton, Fla.; 1993).
38. Shmeeda, H., Even-Chen, S. & Barenholz, Y. Enzymatic assays for quality control and pharmacokinetics of liposome formulations: Comparison with nonenzymatic conventional methodologies. *Methods Enzymol.* 367, 272-292 (2003).
39. Garbuzenko, O., Barenholz, Y. & Priev, A. Effect of grafted PEG on liposome size and on compressibility and packing of lipid bilayer. *Chem. Phys. Lipids* 135, 117-129 (2005).
40. Merkher, Y. et al. A rational human joint friction test using a human cartilage-on-cartilage arrangement. *Tribol. Lett.* 22, 29-36 (2006).
41. Barenholz, Y. Relevancy of drug loading to liposomal formulation therapeutic efficacy. *J. Liposome Res.* 13, 1 (1993).
42. Bligh, E. G. & Dyer, W. J. A rapid method of total lipid extraction and purification. *Can. J. Biochem. Physiol,* 37, 911-917 (1959).
43. Biltonen, R. L. & Lichtenberg, D. The use of differential scanning calorimetry as a tool to characterize liposome preparations. *Chem. Phys. Lipids* 64, 129-142 (1993).
44. Mouritsen, O. G. Life As a Matter of Fat. The Emerging Science of Lipidomics. (Springer-Verlag, Berlin; 2005).
45. Tirosh, O., Barenholz, Y., Katzhendler, J. & Priev, A. Hydration of polyethylene glycol-grafted liposomes. *Biophys. J.* 74, 1371-1379 (1998).

46. Hills, B. A. Boundary lubrication in vivo. *J. Eng. Med.* 214, 83-94 (2000).
47. Mabrey, S. & Sturtevant, J. M. Investigation of phase transitions of lipids and lipid mixtures by high sensitivity differential scanning calorimetry. *PNAS* 73, 3862-3866 (1976).
48. Yoshida, M., Zea-Aragon, Z., Ohtsuki, K., Ohnishi, M. & Ohno, S. Ultrastructural study of upper surface layer in rat mandibular condylar cartilage by quick-freezing method. *Histol. Histopathol.* 19, 1033-1041 (2004).
49. Klein, J. Mechanism of friction across molecularly confined films of simple liquids. *Tribology Series* 36, 59-64 (1999).
50. Maroudas, A. Distribution and diffusion of solutes in articular cartilage. *Biophys. J.* 10, 365-379 (1970).
51. Stockwell, R. A. & Bartlett, C. H. Changes in permeability of articular cartilage with age. *Nature* 201, 835-836 (1964).
52. Barnett, C. H. & Palfrey, A. J. Absorption into the rabbit articular cartilage. *J. Anat.* 99, 365-375 (1965).
53. Faure, C., Bonakdar, L. & Dufourc, E. J. Determination of DMPC hydration in the L(alpha) and L(beta') phases by 2H solid state NMR of D2O. *FEBS Lett.* 405, 263-266 (1997).
54. Schrader, W. et al. Compressibility of lipid mixtures studied by calorimetry and ultrasonic velocity measurements. *J. Phys. Chem. B* 106, 6581-6586 (2002).
55. Schwarz, U.S., Komura, S. & Safran, S. A. Deformation and tribology of multi-walled hollow nanoparticles. *Europhys. Lett.* 50, 762-768 (2000).
56. Parasassi, T., Di Stefano, M., Loiero, M., Ravagnan, G. & Gratton, E. Cholesterol modifies water concentration and dynamics in phospholipid bilayers: a fluorescence study using Laurdan probe. *Biophys J.* 66, 763-768 (1994).
57. Oncins, G., Garcia-Manyes, S. & Sanz, F. Study of frictional properties of a phospholipid bilayer in a liquid environment with lateral force microscopy as a function of NaCl concentration. *Langmuir* 21, 7373-7349 (2005).
58. Ballantine G. C., Stachowiak G. W., The effects of lipid depletion on osteoarthritic wear, *Wear* 253, 385-393 (2002).
59 Jones C. F., Stoffel K., Ozturk H. E., Stachowiak G. W., The effect of surface active phospholipids on the lubrication of osteoarthritic sheep knee joints: wear, *Tribal. Lett.* 16(4), 291-296 (2004).
60 Hills B. A., Monds M. K., Deficiency of lubricating surfactant lining the articular surfaces of replaced hips and knees, *Br. J. Rheumatol.* 37, 143-147 (1998).
61 Freeman M. A. R. (Ed.), Adult Articular Cartilage, 2$^{nd}$ ed., Chapter 3 Pitman Medical, London (1979).
62 Farndale R. W., Buttle D J., Barrett A. J., Improved quantification and discrimination of sulfated glycosaminoglycans by use of dimethylmethylene, Biochim Biophys Acta 883(2), 173-177 (1986).
63. International patent application publication No. WO2003/000190;
64. International patent application publication No. WO2004/047792;
65. International patent application publication No. WO2002/078445

The invention claimed is:

1. A method for lubricating a joint of a mammal, the method comprising: administering into a cavity of the joint having a first temperature a composition consisting essentially of liposomes, wherein said liposomes are multilamellar vesicles (MLV) dispersed in a fluid medium, the liposomes having a mean diameter of between about 0.8 µm to about 10 µm and consisting essentially of membranes including at least one phospholipid (PL) selected from the group consisting of dimyristoylphosphatidylcholine (DMPC) and a mixture of DMPC and dipalmitoyl-phosphatidylcholine (DPPC), the membranes having a phase transition temperature in which solid ordered (SO) to liquid disordered (LD) phase transition occurs, the phase transition temperature being at a temperature of about 20° C. to about 39° C.; the phase transition temperature being lower than the first temperature.

2. The method of claim 1, wherein said PL is dimyristoylphosphatidylcholine (DMPC).

3. The method of claim 1, wherein said PL is the mixture of DMPC and DPPC.

4. The method of claim 3, wherein the ratio of DMPC to DPPC is at least 0.6/1.0 (mole/mole).

5. The method claim 1, wherein said liposomes do not include a membrane active sterol.

6. The method of claim 1, for the treatment of or prevention of an articular disorder or symptoms arising therefrom or for the treatment, management or prevention of deterioration of locked joints, sports injury or traumatic injury towards osteoarthritis (OA).

7. The method of claim 6, wherein said articular disorder is selected from arthritis, osteoarthritis, osteoarthritis in rheumatoid arthritis patients, traumatic joint injury, locked joint, sports injury, status post arthrocentesis, arthroscopic surgery, open joint surgery, and joint replacement.

8. A method for reducing or preventing a mammal's cartilage wear, the method comprising: administering into a cavity of a mammal's joint having a first temperature a composition consisting essentially of liposomes, wherein said liposomes are multilamellar vesicles (MLV) dispersed in a fluid medium, the liposomes having a mean diameter of between about 0.8 µm to about 10 µm and consisting essentially of membranes including at least one phospholipid (PL) selected from the group consisting of dimyristoylphosphatidylcholine (DMPC) and a mixture of DMPC and dipalmitoyl-phosphatidylcholine (DPPC), the membranes having a phase transition temperature in which solid ordered (SO) to liquid disordered (LD) phase transition occurs, the phase transition temperature being at a temperature of about 20° C. to about 39° C.; the phase transition temperature being lower than the first temperature.

9. The method of claim 8, wherein said PL is dimyristoylphosphatidylcholine (DMPC).

10. The method of claim 8, wherein said PL is the mixture of DMPC and DPPC.

11. The method of claim 10, wherein the ratio of DMPC to DPPC is at least 0.6/1.0 (mole/mole).

12. The method claim 8, wherein said liposomes do not include a membrane active sterol.

13. The method of claim 8, for the treatment of or prevention of an articular disorder or symptoms arising therefrom or for the treatment, management or prevention of deterioration of locked joints, sports injury or traumatic injury towards osteoarthritis (OA).

14. The method of claim 13, wherein said articular disorder is selected from arthritis, osteoarthritis, osteoarthritis in rheumatoid arthritis patients, traumatic joint injury, locked joint, sports injury, status post arthrocentesis, arthroscopic surgery, open joint surgery, and joint replacement.

15. The method of claim 1, wherein the liposomes do not include dextran.

16. The method of claim 8, wherein the liposomes do not include dextran.

17. A method for lubricating a joint of a mammal for reducing or preventing cartilage wear, the method comprising:

selecting phospholipids that form liposomes having a phase transition temperature that is in the range of about 20° C. to about 39° C.;

forming a composition consisting essentially of liposomes of multilamellar vesicles (MLV) dispersed in a fluid medium and having a mean diameter of between about 0.8 μm to about 10 μm, wherein the liposomes are formed from phospholipid (PL) membranes consisting essentially of dimyristoylphosphatidylcholine (DMPC) or a mixture of DMPC and another PL, provided that in the mixture the DMPC and other PL are present in a ratio of at least 0.6/1.0 (mole/mole) and that the membranes have a phase transition temperature in which solid ordered (SO) to liquid disordered (LD) phase transition occurs in the in the selected range of about 20° C. to about 39° C.; and administering the selected compositions into a cavity of the joint, wherein the joint has a first temperature and the phase transition temperature of the selected composition is lower than the first temperature.

\* \* \* \* \*

UNITED STATES PATENT AND TRADEMARK OFFICE
CERTIFICATE OF CORRECTION

| | | |
|---|---|---|
| PATENT NO. | : 8,895,054 B2 | Page 1 of 1 |
| APPLICATION NO. | : 12/411855 | |
| DATED | : November 25, 2014 | |
| INVENTOR(S) | : Barenholz et al. | |

It is certified that error appears in the above-identified patent and that said Letters Patent is hereby corrected as shown below:

<u>On the Title Page:</u>
Item (57) ABSTRACT, line 6, change "$C_{12}$-$C_{15}$" to -- $C_{12}$-$C_{18}$ --.

Signed and Sealed this
Twenty-fourth Day of February, 2015

Michelle K. Lee
*Deputy Director of the United States Patent and Trademark Office*